United States Patent [19]

Krumkalns et al.

[11] Patent Number: 4,552,886

[45] Date of Patent: Nov. 12, 1985

[54] FUNGICIDAL PYRIDYLMETHYL-AMINES

[75] Inventors: Eriks V. Krumkalns, Indianapolis; David L. Smiley, Greenfield, both of Ind.

[73] Assignee: Eli Lilly and Company, Indianapolis, Ind.

[21] Appl. No.: 472,439

[22] Filed: Mar. 7, 1983

Related U.S. Application Data

[63] Continuation-in-part of Ser. No. 385,602, Jun. 7, 1982, abandoned.

[51] Int. Cl.[4] .................. C07D 417/12; C07D 413/12; A61K 31/44
[52] U.S. Cl. .................................... 514/342; 514/340; 546/275; 546/280
[58] Field of Search ................ 546/280, 275; 424/263; 514/340, 342

[56] References Cited

U.S. PATENT DOCUMENTS 3,681,367  8/1972  Lee ..................................... 546/275

FOREIGN PATENT DOCUMENTS 2504252  8/1975  Fed. Rep. of Germany ...... 546/280

OTHER PUBLICATIONS

Lin et al., "The Synthesis of Substituted 2-Aminothiazoles", J. Het. Chem. 16, 1377 (1979).
Derwent Abstract 57439W.

Primary Examiner—Alan L. Rotman
Attorney, Agent, or Firm—Bruce J. Barclay; Kathleen R. S. Page; Arthur R. Whale

[57] ABSTRACT

N-Thiazolyl heterocyclic amines, useful as fungicides and aquatic plant growth regulators.

54 Claims, No Drawings

FUNGICIDAL PYRIDYLMETHYL-AMINES

CROSS REFERENCE TO RELATED APPLICATION

This is a continuation-in-part of Ser. No. 385,602, filed June 7, 1982 now abandoned.

SUMMARY OF THE INVENTION

The present invention relates to a compound of the formula

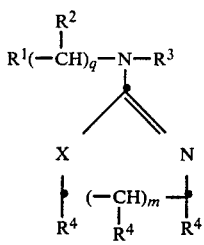

wherein:
$R^1$ is

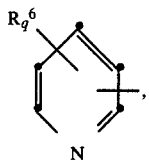 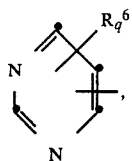

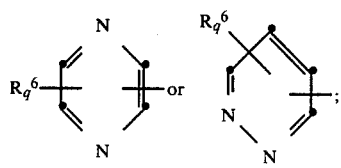

$R^2$ is hydrogen, $C_1$–$C_4$ alkyl or

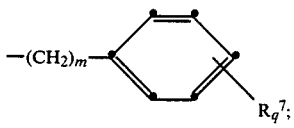

$R^3$ is $C_1$–$C_{10}$ alkyl, $C_2$–$C_{10}$ alkenyl, $C_1$–$C_{10}$ alkoxy, $C_1$–$C_{10}$ haloalkyl, $C_1$–$C_{10}$ haloalkoxy, $C_3$–$C_8$ cycloalkyl, 1,3-benzodioxolyl or

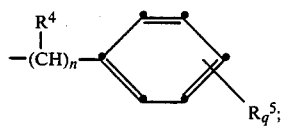

each $R^4$ is independently hydrogen or $C_1$–$C_4$ alkyl;
each $R^5$ is independently $C_1$–$C_6$ alkyl, $C_1$–$C_6$ alkoxy, $C_3$–$C_8$ cycloalkyl, $C_1$–$C_6$ alkylthio, halogen, $C_1$–$C_6$ haloalkyl, $C_1$–$C_6$ haloalkoxy, nitro, cyano or

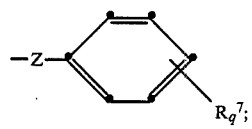

each $R^6$ is independently halogen, $C_1$–$C_4$ alkyl, $C_1$–$C_4$ haloalkyl or $C_1$–$C_4$ haloalkoxy;
each $R^7$ is independently $C_1$–$C_6$ alkyl, $C_1$–$C_6$ alkoxy, $C_3$–$C_8$ cycloalkyl, $C_1$–$C_6$ alkylthio, halogen, $C_1$–$C_6$ haloalkyl, $C_1$–$C_6$ haloalkoxy, nitro or cyano;
X is O or S;
Z is O, S, —$(CH_2)_n$— or a direct link;
each m is independently 0 or 1;
each n is independently 0, 1, 2 or 3;
each q is independently 0, 1 or 2;
and the agronomically-acceptable salts thereof.

The present invention also provides methods of use for the compounds as plant fungicides and aquatic plant growth regulators, as well as compositions containing the present compounds.

DETAILED DESCRIPTION OF THE INVENTION

In the above formula, $C_1$–$C_{10}$ alkyl includes methyl, ethyl, n-propyl, isopropyl, n-butyl, sec.-butyl, isobutyl, t-butyl, n-pentyl, isopentyl, sec.-pentyl, neopentyl, n-hexyl, sec.-hexyl, isohexyl, n-heptyl, isoheptyl, sec.-heptyl, n-octyl, sec.-octyl, isooctyl, n-nonyl, sec.-nonyl, isononyl, n-decyl, sec.-decyl, and the like.

$C_2$–$C_{10}$ Alkenyl is a $C_2$–$C_{10}$ alkyl group containing one carbon-carbon double bond. Such $C_2$–$C_{10}$ alkenyl groups include vinyl, allyl, propenyl, 1-butenyl, isobutenyl, 3,3-dimethyl-1-butenyl, 4-methyl-2-pentenyl, 4-heptenyl, 3-octenyl, 5-decenyl, and the like.

$C_3$–$C_8$ Cycloalkyl represents saturated monocyclic cycloalkyl groups such as cyclopropyl, cyclobutyl, cyclopentyl, cyclohexyl, cycloheptyl, and cyclooctyl.

$C_1$–$C_{10}$ Alkoxy includes methoxy, ethoxy, n-propoxy, isopropoxy, n-butoxy, sec.-butoxy, isobutoxy, t-butoxy, n-pentoxy, isopentoxy, sec.-pentoxy, t-pentoxy, n-hexyloxy, sec.-hexyloxy, isohexyloxy, t-hexyloxy, and the like.

$C_1$–$C_6$ Alkylthio includes methylthio, ethylthio, n-propylthio, isopropylthio, t-butylthio, n-pentylthio, neopentylthio, n-heptylthio, and the like.

The terms "halogen" or "halo" represent fluorine, chlorine, bromine and iodine.

$C_1$–$C_{10}$ Haloalkyl is a $C_1$–$C_{10}$ alkyl group bearing one or more halogen substituents. Such haloalkyl groups include trifluoromethyl, pentafluoroethyl, 1-iodo-2,2,2-trifluoroethyl, 3-chloropropyl, 2-iodopropyl, 2-fluoro-2-methylpropyl, 1-iodobutyl, 4-chloropentyl, 3-fluorohexyl, 3-fluorooctyl, 6-chlorodecyl and the like. $C_1$–$C_6$ haloalkyl is preferred.

$C_1$–$C_{10}$ Haloalkoxy includes trifluoromethoxy, 1-bromoethoxy, 1,1,2,2-tetrafluoroethoxy, 2,2,2-trifluoroethoxy, pentafluoroethoxy, 5,5,5-trifluoropentoxy, 4-chlorohexyloxy, and the like. $C_1$–$C_6$ haloalkoxy is preferred.

Pyridyl represents 2-, 3- or 4-pyridyl; pyrimidinyl represents 2-, 4- or 5-pyrimidinyl; pyrazinyl represents 2-pyrazinyl; and pyridazinyl represents 3- or 4-pyridazinyl.

Agronomically-acceptable salts provided by this invention include both acid addition salt, such as hydrochlorides, hydroiodides, hydrobromides, and the like, and quaternary ammonium salts such as methyl iodides, ethyl iodides, and methyl bromides.

The compounds listed below are typical of the compounds provided by the present invention. It will be understood that the compounds specifically named herein do not bound the scope of the invention, but are presented merely to assure that agricultural chemists will fully understand this invention.

N-[4-(1,1,2,2-Tetrafluoroethoxy)phenyl]-N-(4,5-dihydro-2-thiazolyl)-[(3-pyridyl)methyl]amine
N-(n-Octyl)-N-(4,5-dihydro-2-thiazolyl)-[1-(4-pyridyl)ethyl]amine
N-(3-Methylhexyl)-N-(4,5-dihydro-5-ethyl-2-thiazolyl)-[(3-pyridyl)methyl]amine
N-(6-Chlorohexyl)-N-(4,5-dihydro-2-thiazolyl)-[(3-pyridyl)methyl]amine
N-(3,3-Difluoropropyl)-N-(4,5-dihydro-2-oxazolyl)-[(3-pyridyl)methyl]amine
N-(Heptyloxy)-N-(4,5-dihydro-4-propyl-2-thiazolyl)-[(2-pyridyl)methyl]amine
N-(3,5-Dinitrophenyl)-N-(4,5-dihydro-2-thiazolyl)-[(2-pyrazinyl)methyl]amine
N-(2-Methylthio-5-methylphenyl)-N-(4,5-dihydro-2-thiazolyl)-[1-(5-pyrimidinyl)propyl]amine
N-[4-(t-Butyl)phenyl]-N-(4,5-dihydro-4,5-diethyl-2-thiazolyl)-[(4-pyridazinyl)methyl]amine
N-(3,4-Dichlorophenyl)-N-(4,5-dihydro-2-thiazolyl)-[(3-pyridyl)methyl]amine hydrochloride
N-(4-Cyanophenyl)-N-(4,5-dihydro-2-thiazolyl)[(3-pyridyl)methyl]amine
N-Phenyl-N-(4,5-dihydro-2-oxazolyl)-[(2-pyrimidinyl)methyl]amine
N-(4-Chlorophenyl)-N-(4,5-dihydro-2-thiazolyl)[(3-[5-chloropyridyl])methyl]amine
N-(2,4-Dichlorophenyl)-N-(4,5-dihydro-2-thiazolyl)-[(5-[2-methylpyrimidinyl])methyl]amine
N-(2-Chloro-4-methylphenyl)-N-(4,5-dihydro-2-thiazolyl)-[(3-[4,5-diethylpyridyl])methyl]amine
N-(2-Methyl-4-chlorophenyl)-N-(4,5-dihydro-2-thiazolyl)-[(3-[2-chloro-5-methylpyridyl])methyl]amine
N-(4-Fluorophenyl)-N-(4,5-dihydro-2-thiazolyl)-[1-(3-[5-methylpyridazinyl])ethyl]amine
N-[4-(4-Chlorophenoxy)phenyl]-N-(4,5-dihydro-2-thiazolyl)-[(3-pyridyl)methyl]amine
N-[4-(2-Methyl-4-chlorophenoxy)phenyl]-N-(4,5-dihydro-2-thiazolyl)-[(3-pyridyl)methyl]amine Preferred compounds of the invention have the above formula wherein X is S. N-Thiazolylheterocyclic methaneamines are also preferred.

A particularly preferred group of compounds provided by this invention have the above formula wherein n is 0, $R^1$ is pyridyl and $R^3$ is phenyl or substituted phenyl. Especially preferred compounds have the above formula wherein m is 0, $R^1$ is 3-pyridyl and $R^3$ is phenyl substituted with one or two halogen or alkyl substituents.

Other preferred classes of compounds have the above formula wherein $R^1$ is pyrimidinyl, pyrazinyl or pyridazinyl, m and n are 0 and $R^3$ is substituted phenyl.

The compounds of the present invention may be prepared by methods employing known starting materials that are readily available. The disubstituted amine that is employed as a starting material can be prepared by reacting an appropriately substituted amine with a carbonyl derivative to form a Schiff base, and then reducing the Schiff base by known procedures, preferably by a palladium on carbon catalyzed hydrogenation reaction or by using sodium borohydride in alcohol. This amine starting material may also be prepared by reacting a primary amine with a halogen derivative again according to standard procedures. The scheme for these reactions is as follows:

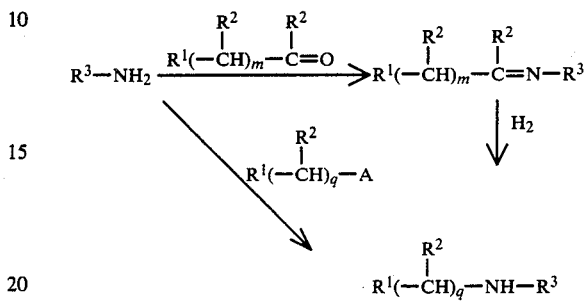

wherein $R^1$, $R^2$, $R^3$, m and q are as defined above and A is a good leaving group such as halogen.

For compounds of the present invention where at least one of $R^2$ is hydrogen, the starting amine may be prepared by acylating an appropriate primary amine to provide the corresponding amide which is reduced to the secondary amine starting material. The scheme for this reaction is as follows:

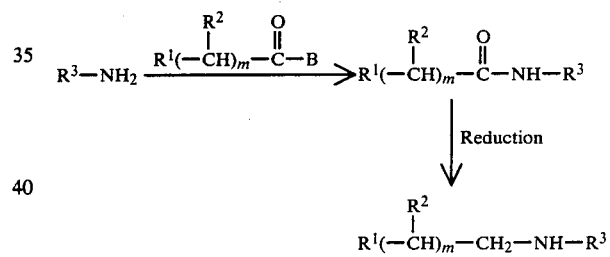

wherein $R^1$, $R^2$, $R^3$ and m are as defined above and B is a good leaving group such as halogen, —O—($C_1$-$C_4$ alkyl) or

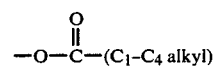

and the like.

The compounds of the present invention may be prepared by procedures well known to those skilled in the art. The preferred synthetic process involves reacting the disubstituted amine starting material, or its alkali metal derivative, with an appropriate isothiocyanate analog to give a compound of the invention. The scheme for this reaction is as follows:

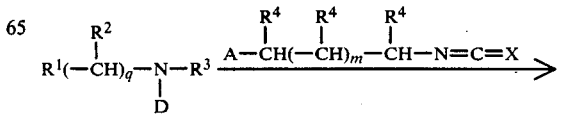

-continued

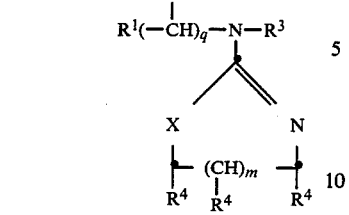

wherein R¹, R², R³, R⁴, m, q and X are as defined above, A is halogen and D is hydrogen or an alkali metal such as sodium or lithium. This procedure is generally carried out by reacting approximately equimolar quantities of the amine and isothiocyanate analogs in an aprotic solvent and at a temperature in the range of from about 0° C. to about 150° C. The preferred temperature range is from about 25° C. to the reflux temperature of the reaction mixture. A base such as triethylamine is preferably added to the mixture to promote the reaction process when D is hydrogen in the above reaction scheme. Suitable aprotic solvents include ethyl acetate, chloroform, dichloromethane, benzene and the like. Chloroform and ethyl acetate are preferred. The product is usually formed after about 1 hour to about 3 days depending on the specific reactants involved. The reaction mixture is then worked up according to procedures well known in the art. Typically, either the solid is filtered off and the filtrate is evaporated under reduced pressure or the reaction mixture is diluted with water and the organic phase separated, dried and concentrated under vacuum. If desired the product may then be further purified by standard procedures such as crystallization or column chromatography over silica gel.

Another similar process which may be used to prepare compounds of the invention involves reacting the disubstituted amine starting material with an alkene isothiocyanate derivative to provide a urea derivative, which can then be cyclized in acid according to the following reaction scheme:

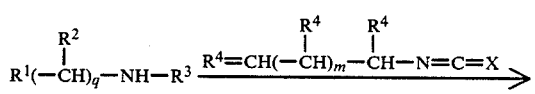

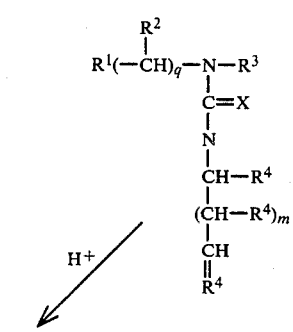

-continued

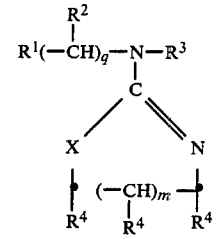

The reaction of the disubstituted amine with the alkene isothiocyanate derivative is performed as outlined above. The cyclization of the compound in acid can also be performed by procedures well known to those skilled in the art. Typical acids suitable for use in this reaction include hydrochloric, hydrobromic, hydroiodic and the like. The reaction occurs at a temperature in the range of from about 25° C. to about 200° C., more preferably at about 75° C. to 125° C. After the reaction is complete, which may take from 1 hour to 10 days, the mixture is generally made basic. The product may then be either collected by filtration or extracted with a water immiscible solvent such as chloroform or ethyl acetate. The product may then be further purified by desired by crystallization, column chromatography or other like procedures.

The N-alkali metal derivative of the disubstituted amine starting material described above may also be alkylated directly with the 2-halogen substituted 5- or 6-membered heterocyclic ring as described below.

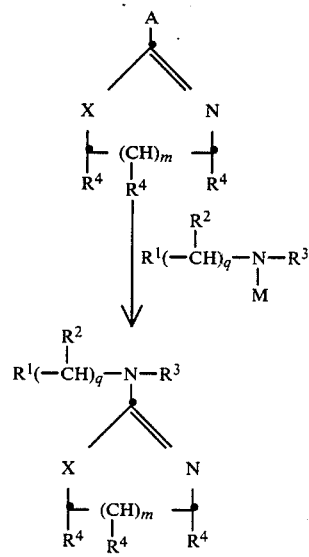

wherein A is a good leaving group such as halogen and M is an alkali metal such as lithium or potassium. This reaction is typically carried out in a suitable solvent and at a low temperature in an inert atmosphere. Suitable solvents should be water-free and include the aprotic solvents, preferably diethyl ether and tetrahydrofuran. The temperature range of the reaction mixture may be from about 20° C. to −100° C. with 0° C. to −20° C. being preferred. The reaction is substantially complete after 10 minutes to 24 hours. The isolated product may then be purified if desired by standard techniques.

An alternative procedure for preparing the compounds of the invention involves beginning with an appropriately substituted 5- or 6-membered heterocyclic amine. For example, the heterocyclic amine may be directly alkylated in two steps to afford a compound of the invention. The scheme for this reaction is as follows:

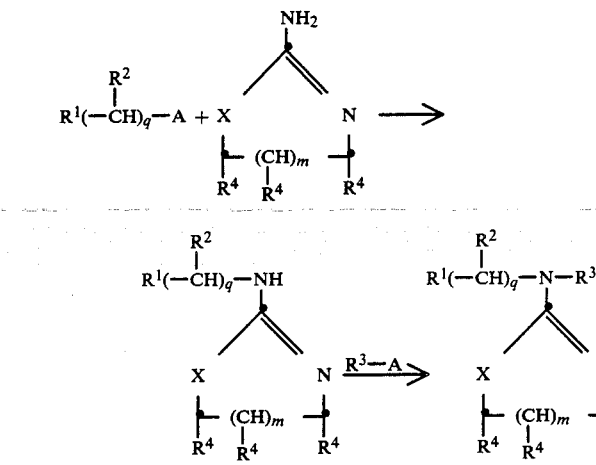

wherein $R^1$, $R^2$, $R^3$, $R^4$, m, q and A are as defined above with the provisos that $R^3$ is other than phenyl or substituted phenyl and q is other than 0. The procedure used to prepare compounds of the invention by this alternative process involves standard alkylation techniques readily known to those skilled in the art. Either step of the reaction can be carried out by combining approximately equimolar quantities of the starting materials in a mutual solvent such as tetrahydrofuran, diethyl ether, dichloromethane, dioxane, dimethylsulfoxide, dimethylformamide, benzene, toluene and the like. Generally a base is also used in the reaction as an acid scavenger. Commonly used bases include sodium carbonate, potassium carbonate, sodium hydroxide, triethylamine and related bases. The reaction generally is substantially complete after about two to about 200 hours when carried out at a temperature of about 20° to about 200° C., preferably from about 30° to about 100° C. The product of the reaction may be isolated by simply removing the reaction solvent, for instance by evaporation under reduced pressure. Also, the reaction mixture may be added to water and the product collected by filtration or extracted into a water immiscible solvent. The product thus isolated can be further purified if desired by any of several well known techniques.

Because all of the compounds comprehended by this invention are amines, the compounds are basic in nature and readily form salts at the amine nitrogen atom. The salt may also form at the nitrogen atom in the $R^1$ substituent as defined above. However, the present compounds are not limited by the position on the compound the salt is formed, as the present invention includes all salts regardless of the form they take. Salts are typically formed by reacting a compound of the invention with an equimolar or excess amount of acid or lower alkyl alkylating agent. The reactants are generally combined in a mutual solvent such as diethyl ether or benzene, and the salt normally precipitates out of solution within about one hour to 10 days, and can be isolated by filtration.

The following detailed examples are provided in an effort to more fully illustrate specific aspects of this invention. The examples are not intended to be limiting in any respect and should not be so construed. In addition to the given physical data, infrared spectroscopy (IR) was performed for certain of these compounds as well. Each compound structure was verified by nuclear magnetic resonance (NMR).

EXAMPLE 1

N-[2-(1,1,2,2-Tetrafluoroethoxy)phenyl]-N-(4,5-dihydro-2-thiazolyl)-[(3-pyridyl)methyl]amine A. N-[2-(1,1,2,2-Tetrafluoroethoxy)phenyl]-[(3-pyridyl)methyl]imine To 32.0 g. of 2-(1,1,2,2-tetrafluoroethoxy)aniline and 17.0 g. of 3-pyridinecarboxaldehyde dissolved in 200 ml. of toluene was added a catalytic amount of p-toluenesulfonic acid. The reaction mixture was refluxed for 6 hours and the water formed as a by-product of the reaction was collected with a Dean-Stark trap. The solution was filtered hot and the filtrate was concentrated under vacuum to afford 49.0 g. of residue. The product appeared as one spot on thin layer chromatography and was used directly in the following reaction.

B. N-[2-(1,1,2,2-Tetrafluoroethoxy)phenyl]-[(3-pyridyl)methyl]amine

To 45.0 g. of N-[2-(1,1,2,2-tetrafluoroethoxy)phenyl]-[(3-pyridyl)methyl]imine dissolved in 250 ml. of ethanol was added 6.0 g. of sodium borohydride. The reaction mixture was stirred overnight at room temperature and then concentrated under vacuum. The residue was slurried in 100 ml. of water and extracted with large volume of ether. The ether extracts were combined and again washed with water. The organic phase was dried over anhydrous sodium sulfate, filtered and concentrated under vacuum. The product precipitated as a white solid from ether/Skellysolve B.

M.P.=49°–50° C.

Analysis calculated for $C_{14}H_{12}F_4N_2O$: Theory: C, 56.00; H, 4.03; N, 9.33; Found: C, 55.77; H, 4.06; N, 9.27.

C. To 9.0 g. of N-[2-(1,1,2,2-tetrafluoroethoxy)phenyl]-[(3-pyridyl)methyl]amine and 4.0 g. β-chloroethylisothiocyanate dissolved in 50 ml. chloroform was added 3.0 g. of triethylamine. The solution was allowed to stir at room temperature overnight and then heated to reflux for about 4 hours. The mixture was cooled and diluted with chloroform. The organic phase was washed with water, dried over anhydrous magnesium sulfate and concentrated under vacuum. The residue was chromatographed over silica gel to provide 3.0 g. of N-[2-(1,1,2,2-tetrafluoroethoxy)phenyl]-N-(4,5-dihydro-2-thiazolyl)-[(3-pyridyl)methyl]amine as an oil. Yield 29%.

NMR: triplet at δ 3.3 (2 protons); triplet at δ 4.1 (2 protons); singlet at δ 5.0 (2 protons); triplet at δ 6.0 (1 proton); multiplet at δ 7.3 (5 protons); and singlet at δ 8.5 (2 protons).

EXAMPLE 2

N-(4-Chlorophenyl)-N-(4,5-dihydro-5-methyl-2-thiazolyl)-[(3-pyridyl)methyl]amine A. N-(4-Chlorophenyl)-N'-(2-propenyl)-N-[(3-pyridyl)methyl]thiourea To 4.7 g. of N-(4-chlorophenyl)-[(3-pyridyl)methyl]amine dissolved in chloroform was added 3.1 ml. of allyl isothiocyanate. The reaction mixture was stirred at room temperature for approximately 48 hours. The mixture was then refluxed for an additional 48 hours and cooled to room temperature. The volatiles were removed under vacuum and the residue was crystallized from diethyl ether to afford 6.1 g. of N-(4-chlorophenyl)-N'-(2-propenyl)-N-[(3-pyridyl)methyl]thiourea. Yield 89%.

M.P.=131°-134° C.

Analysis calculated for $C_{16}H_{16}ClN_3S$: Theory: C, 60.46; H, 5.07; N, 13.22; Found: C, 60.25; H, 5.24; N, 13.04.

B. A solution 3.6 g. of N-(4-chlorophenyl)N'-(2-propenyl)-N-[(3-pyridyl)methyl]thiourea dissolved in 6 N HCl was heated to near boiling. The mixture was poured into a solution of 50% NaOH and ice, extracted with ethyl acetate, dried and concentrated under vacuum. The product was purified over silica gel to afford 2.3 g. of N-(4-chlorophenyl)-N-(4,5-dihydro-5-methyl-2-thiazolyl)-[(3-pyridyl)methyl]amine. Yield 64%.

Analysis calculated for $C_{16}H_{16}ClN_3S$: Theory: C, 60.46; H, 5.07; N, 13.22; Found: C, 60.23; H, 5.14; N, 13.22.

EXAMPLE 3

N-(1-Methylhexyl)-N-(4,5-dihydro-2-thiazolyl)[(3-pyridyl)methyl]amine

To 3.1 g. of N-(1-methylhexyl)-[(3-pyridyl)methyl]amine dissolved in approximately 20 ml. of ethanol-free chloroform was added 1.8 g. of 2-chloroethylisothiocyanate followed by 2.08 ml. of triethylamine. The reaction mixture was stirred at room temperature overnight and then refluxed for approximately 4 hours. The solvent was evaporated under reduced pressure and the residue was chromatographed over silica gel while eluting with chloroform/acetone to afford approximately 4.0 g. of the desired product. Yield 91%.

Analysis calculated for $C_{16}H_{25}N_3S$: Theory: C, 65.94; H, 8.65; N, 14.42; Found: C, 65.71; H, 8.45; N, 14.19.

EXAMPLE 4

N-(4-Chlorophenyl)-N-(4,5,6-trihydro-2-thiazinyl)-[(3-pyridyl)methyl]amine

To 5.5 g. of N-(4-chlorophenyl)-[(3-pyridyl)methyl]amine dissolved in 50 ml. of ethyl acetate was added 5.4 g. of 3-bromopropylisothiocyanate and 4.16 ml. of triethylamine. The mixture was heated slightly for approximately 4 days and cooled. The solid was collected by filtration and washed with ethyl acetate. The filtrate was concentrated under vacuum and the resulting residue was chromatographed to afford 8.2 g. of an oil. The oil was dissolved in ethyl acetate and washed twice with water. The organic phase was dried over anhydrous magnesium sulfate, filtered, and concentrated under vacuum. The resulting oil crystallized on setting and was triturated with petroleum ether. The precipitated solid was collected by filtration and dried in vacuo to give 2.1 g. of N-(4-chlorophenyl)-N-(4,5,6-trihydro-2-thiazinyl)-[(3-pyridyl)methyl]amine. Yield 26%.

Analysis calculated for $C_{16}H_{16}ClN_3S$: Theory: C, 60.46; H, 5.07; N, 13.22; Found: C, 60.29; H, 5.14; N, 12.99.

EXAMPLE 5

N-(4-Chlorophenyl)-N-(4,5-dihydro-2-oxazolyl)[(3-pyridyl)methyl]amine

To a solution of 4.37 g. of N-(4-chlorophenyl)-[(3-pyridyl)methyl]amine dissolved in 30 ml. of ethyl acetate was added 2.3 g. of 2-chloroethylisocyanate. The reaction mixture was heated for approximately 72 hours at which point 2 to 3 additional drops of the isocyanate were added. After 48 more hours of heating, the ethyl acetate was removed in vacuo. The residue was combined with 20 ml. of water and 2.9 ml. of triethylamine and the mixture was refluxed for approximately 30 minutes. An oil precipitated as the reaction mixture cooled and was extracted with chloroform. The organic phase was dried over anhydrous magnesium sulfate, filtered and concentrated in vacuo. The residue was chromatographed over silica gel while eluting with chloroform/acetone. The appropriate fractions were combined to afford 3.2 g. of N-(4-chlorophenyl)-N-(4,5-dihydro-2-oxazolyl)-[(3-pyridyl)methyl]amine. Yield 56%.

Analysis calculated for $C_{15}H_{14}ClN_3O$: Theory: C, 62.61; H, 4.90; N, 14.60; Found: C, 62.48; H, 5.05; N, 14.37.

The following examples further exemplify the compounds of the present invention and were prepared by the general procedure outlined in Example 1 above.

EXAMPLE 6

N-(1,3-Benzodioxol-5-yl)-N-(4,5-dihydro-2-thiazolyl)-[(3-pyridyl)methyl]amine

M.P.=92°-95° C.

Analysis calculated for $C_{16}H_{15}N_3O_2S$: Theory: C, 61.32; H, 4.82; N, 13.41; Found: C, 61.05; H, 4.89; N, 13.15.

EXAMPLE 7

N-(4-Chlorophenyl)-N-(4,5-dihydro-2-thiazolyl)-[1-(3-pyridyl)ethyl]amine

Oil

Analysis calculated for $C_{16}H_{16}ClN_3S$: Theory: C, 60.46; H, 5.07; N, 13.22; Found: C, 60.31; H, 5.14; N, 13.48.

EXAMPLE 8

N-(2,4-Dichlorophenyl)-N-(4,5-dihydro-2-thiazolyl)-[(3-pyridyl)methyl]amine

Oil

NMR: triplet at δ 3.3 (2 protons); triplet at δ 4.1 (2 protons); singlet at δ 4.9 (2 protons); multiplet at δ 7.3 (5 protons); and singlet at 67 8.5 (2 protons).

EXAMPLE 9

N-(4-Chlorophenyl)-N-(4,5-dihydro-2-thiazolyl)[(2-pyridyl)methyl]amine

Oil

Analysis calculated for $C_{15}H_{14}ClN_3S$: Theory: C, 59.30; H, 4.64; N, 13.83; Found: C, 59.23; H, 4.64; N, 13.95.

EXAMPLE 10

N-(4-Chlorophenyl)-N-(4,5-dihydro-4-methyl-2-thiazolyl)-[(3-pyridyl)methyl]amine Oil Analysis calculated for $C_{16}H_{16}ClN_3S$: Theory: C, 60.46; H, 5.07; N, 13.22; Found: C, 60.21; H, 5.01; N, 12.96.

EXAMPLE 11

N-(4-Chlorophenyl)-N-(4,5-dihydro-2-thiazolyl)[(4-pyridyl)methyl]amine

Oil

Analysis calculated for $C_{15}H_{14}ClN_3S$: Theory: C, 59.30; H, 4.64; N, 13.83; Found: C, 59.08; H, 4.55; N, 13.59.

EXAMPLE 12

N-Cyclohexyl-N-(4,5-dihydro-2-thiazolyl)-[(3-pyridyl)methyl]amine

Oil

NMR: multiplet at δ 1.0 to 1.8 (10 protons); multiplet at δ 3.0 to 4.2 (5 protons); singlet at δ 4.5 (2 protons); multiplet at δ 7.2 (1 proton); doublet at δ 7.6 (1 proton); and multiplet at δ 8.5 (2 protons).

EXAMPLE 13

N-(4-Chlorophenyl)-N-(4,5-dihydro-2-thiazolyl)[(3-pyridyl)methyl]amine

Oil

Analysis calculated for $C_{15}H_{14}ClN_3S$: Theory: C, 59.31; H, 4.61; N, 13.84; Found: C, 59.52; H, 4.65; N, 13.98.

EXAMPLE 14

N-(2-Chlorophenyl)-N-(4,5-dihydro-2-thiazolyl)[(3-pyridyl)methyl]amine

Oil

NMR: triplet at δ 3.3 (2 protons); triplet at δ 4.2 (2 protons); singlet at δ 5.0 (2 protons); multiplet at δ 7.0 to 7.8 (6 protons); and multiplet at δ 8.5 (2 protons).

EXAMPLE 15

N-(2,6-Dimethylphenyl)-N-(4,5-dihydro-2-thiazolyl)-[(3-pyridyl)methyl]amine
M.P.=90°-92° C.

NMR: singlet at δ 2.0 (6 protons); triplet at δ 3.3 (2 protons); triplet at δ 4.2 (2 protons); singlet at δ 4.9 (2 protons); multiplet at δ 7.2 (4 protons); multiplet at δ 7.8 (1 proton); and doublet at δ 8.5 (2 protons).

EXAMPLE 16

N-(2-Methyl-4-chlorophenyl)-N-(4,5-dihydro-2-thiazolyl)-8 3-pyridyl)methyl]amine Oil Analysis calculated for $C_{16}H_{16}ClN_3S$: Theory: C, 60.46; H, 5.07; N, 13.22; Found: C, 60.23; H, 4.78; N, 13.18.

EXAMPLE 17

N-(2-Methyl-4-methoxyphenyl)-N-(4,5-dihydro-2-thiazolyl)-[(3-pyridyl)methyl]amine Oil NMR: singlet at δ 2.1 (3 protons); triplet at δ 3.3 (2 protons); singlet at δ 3.7 (3 protons); triplet at δ 4.1 (2 protons); doublet at δ 4.5 (1 proton); doublet at δ 5.2 (1 proton); multiplet at δ 6.8 (3 protons); doublet at δ 7.2 (1 proton); doublet at δ 7.7 (1 proton); and singlet at δ 8.5 (2 protons).

EXAMPLE 18

N-(2,4-Dichlorophenyl)-N-(4,5-dihydro-2-thiazolyl)-[(3-pyridyl)methyl]amine
M.P.=95°-96° C.

Analysis calculated for $C_{16}H_{15}Cl_2N_3S$: Theory: C, 54.55; H, 4.29; N, 11.93; Found: C, 54.35; H, 4.22; N, 11.68.

EXAMPLE 19

N-(4-Bromophenyl)-N-(4,5-dihydro-2-thiazolyl)-[(3-pyridyl)methyl]amine
M.P.=72°-74° C.

Analysis calculated for $C_{15}H_{14}ClN_3S$: Theory: C, 51.73; H, 4.05; N, 12.07; Found: C, 52.02; H, 3.90; N, 11.90.

EXAMPLE 20

N-(2,6-Dichlorophenyl)-N-(4,5-dihydro-2-thiazolyl)-[(3-pyridyl)methyl]amine

Oil

NMR: triplet at δ 3.3 (2 protons); triplet at δ 4.2 (2 protons); singlet at δ 5.0 (2 protons); multiplet at δ 7.3 (5 protons); and doublet at δ 8.5 (2 protons).

EXAMPLE 21

N-(2-Chloro-4-methylphenyl)-N-(4,5-dihydro-2-thiazolyl)-[(3-pyridyl)methyl]amine Oil NMR: singlet at δ 2.3 (3 protons); triplet at δ 3.3 (2 protons); doublet at δ 4.2 (2 protons); singlet at δ 4.9 (2 protons); multiplet at δ 7.4 (5 protons); and singlet at δ 8.5 (2 protons).

EXAMPLE 22

N-(2,4-Dimethylphenyl)-N-(4,5-dihydro-2-thiazolyl)-[(3-pyridyl)methyl]amine

Oil

NMR: singlet at δ 2.2 (3 protons); singlet at δ 2.3 (3 protons); triplet at δ 3.3 (2 protons); triplet at δ 4.2 (2 protons); singlet at δ 4.8 (2 protons); multiplet at δ 7.0 (4 protons); doublet at δ 7.6 (1 proton); and singlet at δ 8.4 (2 protons).

EXAMPLE 23

N-(4-Cyclohexylphenyl)-N-(4,5-dihydro-2-thiazolyl)-[(3-pyridyl)methyl]amine

Oil

NMR: multiplet at δ 1.5 (10 protons); singlet at δ 2.5 (1 proton); triplet at δ 3.2 (2 protons); triplet at δ 4.1 (2 protons); singlet at δ 5.0 (2 protons); multiplet of δ 7.1 (5 protons); doublet at δ 7.6 (1 proton); and doublet at δ 8.5 (2 protons).

EXAMPLE 24

N-Phenyl-N-(4,5-dihydro-2-thiazolyl)-[(3-pyridyl)methyl]amine

Oil

NMR: triplet at δ 3.3 (2 protons); triplet at δ 4.1 (2 protons); singlet at δ 5.0 (2 protons); multiplet at δ 7.2 (6 protons); singlet at δ 7.6 (1 proton); singlet at δ 8.5 (2 protons).

EXAMPLE 25

N-[4-(Methylthio)phenyl]-N-(4,5-dihydro-2-thiazolyl)-[(3-pyridyl)methyl]amine

Oil

Analysis calculated for $C_{16}H_{17}N_3S_2$: Theory: C, 60.92; H, 5.43; N, 13.32; Found: C, 60.65; H, 5.57; N, 13.09.

EXAMPLE 26

N-(4-Phenoxyphenyl)-N-(4,5-dihydro-2-thiazolyl)-[(3-pyridyl)methyl]amine

Oil

NMR: triplet at δ 3.3 (2 protons); triplet at δ 4.1 (2 protons); singlet at δ 5.0 (2 protons); multiplet at δ 7.0 (10 protons); doublet at δ 7.6 (1 proton); and doublet at δ 8.5 (2 protons).

EXAMPLE 27

N-(4-Chlorophenyl)-N-(4,5-dihydro-2-thiazolyl)-[(5-pyrimidinyl)methyl]amine

M.P.=87°-94° C.

Analysis calculated for $C_{14}H_{13}ClN_4S$: Theory: C, 55.17; H, 4.30; N, 18.38; Found: C, 55.34; H, 4.20; N, 18.51.

EXAMPLE 28

N-(2,6-Difluorophenyl)-N-(4,5-dihydro-2-thiazolyl)-[(3-pyridyl)methyl]amine

M.P.=62°-63° C.

Analysis calculated for $C_{15}H_{13}F_2N_3S$: Theory: C, 59.02; H, 4.26; N, 13.77; Found: C, 58.52; H, 4.40; N, 13.62.

EXAMPLE 29

N-(4-Fluorophenyl)-N-(4,5-dihydro-2-thiazolyl)-[(2-pyridyl)methyl]amine

M.P.=67°-70° C.

Analysis calculated for $C_{15}H_{14}FN_3S$: Theory: C, 62.72; H, 4.88; N, 14.63; Found: C, 62.48; H, 4.90; N, 14.39.

EXAMPLE 30

N-(4-Chlorophenyl)-N-(4,5-dihydro-2-thiazolyl)-[(2-pyrazinyl)methyl]amine

M.P.=99°-102° C.

Analysis calculated for $C_{14}H_{13}ClN_4S$: Theory: C, 55.17; H, 4.30; N, 18.38; Found: C, 54.91; H, 4.49; N, 18.12.

EXAMPLE 31

N-[(4-Fluorophenyl)methyl]-N-(4,5-dihydro-2-thiazolyl)-(3-pyridyl)amine

M.P.=78° C.

Analysis calculated for $C_{15}H_{14}FN_3S$: Theory: C, 62.20; H, 4.91; N, 14.62; Found: C, 62.45; H, 4.68; N, 14.86.

EXAMPLE 32

N-[2-(4-Chlorophenyl)ethyl]-N-(4,5-dihydro-2-thiazolyl)-[(3-pyridyl)methyl]amine

M.P.=74°-75° C.

Analysis calculated for $C_{17}H_{18}N_3ClS$: Theory: C, 61.53; H, 5.47; N, 12.66; Found: C, 61.45; H, 5.65; N, 12.88.

EXAMPLE 33

N-[1-(4-Fluorophenyl)ethyl]-N-(4,5-dihydro-2-thiazolyl)-[1-(3-pyridyl)ethyl]amine Oil Analysis calculated for $C_{18}H_{20}FN_3S$: Theory: C, 65.63; H, 6.12; N, 12.75; Found: C, 65.46; H, 5.84; N, 12.63.

EXAMPLE 34

N-(3-Chlorophenyl)-N-(4,5-dihydro-2-thiazolyl)[(3-pyridyl)methyl]amine

Oil

Analysis calculated for $C_{15}H_{14}ClN_3S$: Theory: C, 59.30; H, 4.64; N, 13.83; Found: C, 59.08; H, 4.42; N, 13.68.

EXAMPLE 35

N-[(4-Chlorophenyl)methyl]-N-(4,5-dihydro-2-thiazolyl)-(3-pyridyl)amine

Oil

NMR: triplet at δ 3.4 (2 protons); triplet at δ 4.1 (2 protons); singlet at δ 5.0 (2 protons); multiplet at δ 7.4 (6 protons); and doublet at δ 8.5 (2 protons).

EXAMPLE 36

N-(2,4-Dichlorophenyl)-N-(4,5-dihydro-5-methyl-2-thiazolyl)-[(3-pyridyl)methyl]amine Oil Analysis calculated for $C_{16}H_{15}Cl_2N_3S$: Theory: C, 54.55; H, 4.29; N, 11.93; Found: C, 54.93; H, 4.63; N, 12.13.

EXAMPLE 37

N-(2,4-Difluorophenyl)-N-(4,5-dihydro-2-thiazolyl)-[(3-pyridyl)methyl]amine

Oil

Analysis calculated for $C_{15}H_{13}N_3F_2S$: Theory: C, 59.00; H, 4.29; N, 13.76; Found: C, 58.75; H, 4.40; N, 13.57.

EXAMPLE 38

N-(3-Chlorophenyl)-N-(4,5-dihydro-2-thiazolyl)[(3-pyridyl)methyl]amine

Oil

Analysis calculated for $C_{15}H_{14}FN_3S$: Theory: C, 62.72; H, 4.88; N, 14.63; Found: C, 62.80; H, 5.17; N, 14.34.

EXAMPLE 39

N-[3-(Trifluoromethyl)phenyl]-N-(4,5-dihydro-2-thiazolyl)-[(3-pyridyl)methyl]amine Oil Analysis calculated for $C_{16}H_{14}F_3N_3S$: Theory: C, 56.96; H, 4.18; N, 12.46; Found: C, 56.70; H, 4.11; N, 12.24.

EXAMPLE 40

N-(4-Chlorophenyl)-N-(4,5-dihydro-4-methyl-2-thiazolyl)-[1-(3-pyridyl)ethyl]amine Oil Analysis calculated for $C_{17}H_{18}ClN_3S$: Theory: C, 61.53; H, 5.47; N, 12.66; Found: C, 61.38; H, 5.51; N, 12.44.

EXAMPLE 41

N-(3,4-Dichlorophenyl)-N-(4,5-dihydro-2-thiazolyl)-[(3-pyridyl)methyl]amine

Oil

Analysis calculated for $C_{15}H_{13}Cl_2N_3S$: Theory: C, 53.26; H, 3.87; N, 12.42; Found: C, 53.13; H, 3.91; N, 12.21.

EXAMPLE 42

N-(2,4-Dimethylphenyl)-N-(4,5-dihydro-2-thiazolyl)-[(3-pyridyl)methyl]amine monohydrochloride
M.P.=150° C. dec.

EXAMPLE 43

N-(4-Fluorophenyl)-N-(4,5-dihydro-2-thiazolyl)[(3-pyridyl)methyl]amine

Oil

Analysis calculated for $C_{15}H_{14}FN_3S$: Theory: C, 62.70; H, 4.91; N, 14.62; Found: C, 62.56; H, 5.24; N, 14.72.

EXAMPLE 44

N-(4-Cyanophenyl)-N-(4,5-dihydro-2-thiazolyl)[(3-pyridyl)methyl]amine
M.P.=118°-121° C.

Analysis calculated for $C_{16}H_{14}N_4S$: Theory: C, 65.28; H, 4.79; N, 19.03; Found: C, 65.17; H, 4.59; N, 18.81.

EXAMPLE 45

N-(4-Chlorophenyl)-N-(4,5-dihydro-2-thiazolyl)[(3-pyridyl)methylphenyl]amine

NMR: triplet at δ 3.3 (2 protons); triplet at δ 4.1 (2 protons); doublet at δ 6.9 (2 protons); singlet at δ 7.07 (1 proton); multiplet from δ 7.1 to δ 7.2 (6 protons); doublet at δ 7.3 (2 protons); doublet at δ 7.4 (1 proton); doublet at δ 8.47 (1 proton); and singlet at δ 8.54 (1 proton).

EXAMPLE 46

N-(4-Fluorophenyl)-N-(4,5-dihydro-5-methyl-2-thiazolyl)-[(3-pyridyl)methyl]amine Oil Analysis calculated for $C_{16}H_{16}FN_3S$: Theory: C, 63.76; H, 5.35; N, 13.94; Found: C, 63.94; H, 5.14; N, 13.87.

EXAMPLE 47

N-(1,3-Benzodioxol-5-yl)-N-(4,5,6-trihydro-2-thiazinyl)-[(3-pyridyl)methyl]amine
M.P.=90°-93° C.

Analysis calculated for $C_{17}H_{17}N_3O_2S$: Theory: C, 62.37; H, 5.23; N, 12.83; Found: C, 62.10; H, 5.18; N, 12.62.

EXAMPLE 48

N-[1-(4-Chlorophenyl)ethyl]-N-(4,5-dihydro-2-thiazolyl)-[(3-pyridyl)methyl]amine Oil Analysis calculated for $C_{17}H_{18}ClN_3S$: Theory: C, 61.53; H, 5.47; N, 12.66; Found: C, 61.33; H, 5.34; N, 12.47.

EXAMPLE 49

N-[1-(4-Fluorophenyl)ethyl]-N-(4,5-dihydro-2-thiazolyl)-(3-pyridyl)amine
M.P.=65°-68° C.

Analysis calculated for $C_{16}H_{16}FN_3S$: Theory: C, 63.76; H, 5.35; N, 13.94; F, 6.30; Found: C, 63.55; H, 5.30; N, 13.78; F, 6.53.

As noted above, the compounds of this invention have displayed potent activity in the regulation of aquatic plant growth. The concentration of compound present in the body of water to be treated depends on the effect desired and plant species to be treated. Typical aquatic plants that can be controlled include hydrilla (*Hydrilla verticillata*), coontail (*Ceratophyllum demersum L.*), Eurasian watermilfoil (*Myriophyllum specatum L.*), Southern naiad (*Najas quadalupensis Spreng.*), sago pondweed (*Potamogeton pectinatus L.*) and the like. When the compounds of the present invention are added to the water containing submerged and floating aquatic plants for which control is desired, a concentration range of from about 0.10 to about 10 ppm (parts per million) of the active compound is desired. It is, of course, apparent that higher or lower concentrations can be employed depending on the plant species to be controlled, the temperature, shape and type of the body of water to be treated. At higher water temperatures, for example, less compound is generally required for a given degree of control than is needed at lower temperatures.

The following experiment was used in the laboratory to evaluate the aquatic growth regulating properties of the compounds disclosed herein.

EXPERIMENT 1

The compounds for this test were formulated in the following manner. Twenty milligrams of test compound were weighed into a 12 ml. disposable vial. To the vial containing the compound was added 1 ml. of acetone and 9 ml. of aqueous 0.1 percent Tween 80 (polyoxyethylene sorbitan monooleate). This solution was then diluted with appropriate volumes of water to obtain solutions containing 10, 1, 0.5 and 0.25 ppm. of test compound.

Terminal pieces of *Hydrilla verticillata*, (hereinafter identified as hydrilla) 10 cm. long, without branching, were prepared for testing. Three such cuttings were placed in each plastic container holding 785 ml. of water containing the formulated test compound and 3 ml. of Hoagland's nutrient solution. Three 10 cm. cuttings of hydrilla were placed in each of several untreated control containers of water. To the water in each control container there was also added the amount of solvent used to formulate the test compound.

After a period of two to three weeks, measurements were made to determine the total length of each plant. An average total growth was obtained by dividing the total combined lengths by the number of replicates. By subtracting 10 cm. from the average total length, the average increase in growth was obtained. This difference was divided by the average increase in length of the plants in the solvent controls (SC) and the quotient multiplied by 100 to give a percent inhibition, as illustrated below:

$$\frac{\text{Total combined length of Replicates}}{\text{Number of Replicates}} = \text{Average Length}$$

Avg. Length − 10 cm. = Avg. Increased Growth $$\left[1 - \frac{\text{Avg. Increased Growth}}{\text{Avg. Increased Growth } SC}\right] \times 100 = \% \text{ Inhibition}$$

The results of the test, run at the reported concentration levels in ppm. of compound, and observed at the end of three weeks, are set forth in Table 1 which follows.

TABLE 1

AQUATIC GROWTH REGULATOR ACTIVITY

| Example No. of Compound Tested | Approximate % Growth Inhibition of Hydrilla at Indicated Test Concentration | | | |
|---|---|---|---|---|
| | 10 ppm. | 1 ppm. | 0.5 ppm. | 0.25 ppm. |
| 2 | 86 | | | |
| 3 | 95 | 4 | −1 | −12 |
| 4 | 67 | −18 | 0 | −1 |
| 5 | 49 | −4 | −2 | 5 |
| 6 | 32 | | | |
| 7 | 80 | 16 | 1 | 4 |
| 8 | 77,78 | −8 | 0 | 0 |
| 9 | 31 | | | |
| 10 | 90 | 3 | −1 | −23 |
| 11 | 73 | 1 | 12 | −4 |
| 12 | 79 | 7 | 3 | 2 |
| 13 | 90 | −20 | −8 | −24 |
| 14 | −7 | | | |
| 15 | 56 | 5 | 4 | −28 |
| 16 | 87 | | | |
| 17 | 51 | −14 | 4 | −1 |
| 18 | 84 | | | |
| 19 | 77 | | | |
| 20 | | 6 | −18 | −1 |
| 22 | 63 | −3 | −1 | 30 |
| 23 | 100 | 20 | 13 | 18 |
| 24 | 54 | | | |
| 25 | 70 | 1 | 5 | 7 |
| 26 | 83 | 3 | 7 | 8 |
| 27 | 40 | | | |
| 28 | 69 | | | |
| 29 | 35 | −11 | 12 | 4 |
| 30 | 54 | −16 | −6 | 8 |
| 32 | 84 | | | |
| 33 | 57 | −13 | −10 | −7 |
| 34 | 83 | | | |
| 35 | 91 | | | |
| 37 | 58 | −14 | −3 | −3 |
| 38 | 86 | −20 | 18 | 5 |
| 39 | 76 | −19 | −6 | −4 |
| 41 | 80 | −11 | −14 | −4 |
| 42 | 72 | −8 | −3 | 2 |
| 43 | 67 | −5 | −10 | 5 |
| 46 | 57 | | | |
| 48 | 88 | 0 | 5 | −4 |

The compounds of the present invention have also been found to control plant fungal diseases. When employed in the treatment of such plant fungal diseases, the compounds are applied to the plants in a disease inhibiting and non-herbicidal amount. The term "disease inhibiting and non-herbicidal amount," as used herein, refers to an amount of a compound of the invention which kills or stunts the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the particular plant species, climate conditions and the like.

The following experiments were performed in the laboratory to determine the fungicidal efficacy of the compounds of the invention.

EXPERIMENT 2

This initial screen was used to evaluate the efficacy of the compounds against a variety of different agents causing plant diseases.

The test compounds were formulated for application by dissolving 48 mg. of the compound into 1.2 ml. of solvent. The solvent was prepared by mixing 100 ml. of Tween 20 with 500 ml. of acetone and 500 of ethanol. The solvent/compound solution was finally diluted to 120 ml. with deionized water.

The formulated test compounds were applied by both soil drench and foliar methods. In the foliar spray application method the following plant pathogens and their corresponding host plants were employed.

Powdery Mildew—Bean
Anthracnose—Cucumber
Rice Blast—Rice
Botrytis—Grape
Helminthosporium—Wheat
Leaf Rust—Wheat
Late Blight—Tomato The foliar application was conducted at a 400 ppm. test compound concentration by either of two methods. In the botrytis test, the formulated compound was sprayed onto the plants with a small DeVilbiss atomizer at approximately 8 psi. In the remaining tests the formulated test compounds were sprayed by hand in an exhaust ventilated chamber. Single pots of different plant species were placed on raised, revolving pedestals in the chamber. Using a DeVilbiss spray gun, Model TGA-502, all test solutions were applied by hand at 40 psi. As the spray was delivered, the pedestals were rotated to expose all plant surfaces to the spray pattern. The spray was applied to past the run-off point. All treatments were allowed to dry and the host plants were inoculated with the pathogens 24 hours later.

In the soil drench application method the following plant pathogen and host plant was employed.

Rhizoctonia Damping-off—Cotton

The soil drench method was performed by uniformly syringing 20 ml. of the formulation over the soil surface of each pot containing a different crop species. The pot size at the soil surface was 2.0 inches in diameter, thus equalling a test compound concentration of 35 lbs./acre (39.2 kg.ha.).

The effectiveness of test compounds in controlling the foregoing plant diseases was rated on a scale of 1 to 5. On this scale "1" indicates severe disease (or no control), "2" is moderate idsease, "3" is slight disease, "4" is very slight disease and "5" indicates no disease or 100% control. Also a phytotoxicity rating was recorded where present again using a scale from 1 to 5 wherein 1 indicates no toxicity and 5 indicates death to the plant. Finally, where phytotoxicity was present, a letter rating may be given to the plant indicating the type of injury caused to the plant. These injuries were coded as follows:

G = General necrosis
W = Wilting
S = Stunting
C = Chlorosis
F = Formative

Table 2 presents the activity of typical compounds of the present invention when evaluated in the foliar application method described above, while Table 3 presents the results of the soil drench application method.

TABLE 2

Foliar Application

| Example No. of Compound Tested | Powdery Mildew | Anthracnose | Rice Blast | Botrytis | Helminthosporium | Leaf Rust | Late Blight |
|---|---|---|---|---|---|---|---|
| 1 | 5 | 1 | 1 | 1 | 1 | 1 | 1 |
| 2 | 5 | 1 | 1 | 1 | 4 | 1 | 1 |
| 3 | 1 | 1 | 1 | 1 | 1 | 1 | 1 |
| 4 | 5 | 1 | 1 | 1 | 1 | 1 | 1 |
| 5 | 3 | 1 | 1 | 1 | 1 | 1 | 1 |
| 6 | 4 | 1 | 1 | 1 | 1 | 1 | 1 |
| 7 | 5 | 1 | 1 | 1 | 5 | 1 | 1 |
| 8 | 5 | 4 | 1 | 1 | 4 | 3 | 1 |
| 9 | 1 | 1 | 1 | 1 | 1 | 1 | 1 |
| 10 | 5 | 1 | 1 | 1 | 5 | 1 | 1 |
| 11 | 1 | 1 | 1 | 1 | 1 | 1 | 1 |
| 12 | 1 | 1 | 1 | 1 | 1 | 1 | 1 |
| 13 | 5 | 1 | 1 | 1 | 5(2G) | 1 | 1 |
| 14 | 5(2F) | 1 | 1 | 1 | 4 | 1 | 1 |
| 15 | 4 | 1 | 1 | 1 | 4 | 1 | 1 |
| 16 | 5(2F) | 1 | 1 | 1 | 4 | 1 | 1 |
| 17 | 4 | 1 | 1 | 1 | 1 | 1 | 1 |
| 18 | 4(2G) | 1 | 1 | 1 | 5 | 4 | 1 |
| 19 | 5(2G) | 1 | 1 | 1 | 4 | 1 | 1 |
| 20 | 5(2G) | 1 | 1 | 1 | 4 | 1 | 1 |
| 24 | 5(2S) | 1 | 1 | 1 | 4 | 1 | 3 |
| 25 | 1 | 1 | 1 | 1 | 1 | 1 | 1 |
| 26 | 4 | 1 | 1 | 1 | 5 | 1 | 1 |
| 29 | 1 | 1 | 1 | 1 | 1 | 1 | 1 |
| 30 | 4 | 1 | 1 | 1 | 1 | 1 | 1 |
| 31 | 1 | 1 | 1 | 1 | 1 | 1 | 1 |
| 32 | 3 | 1 | 1 | 1 | 4 | 1 | 1 |
| 33 | 1(2G) | 4 | 1 | 1 | 1 | 1 | 1 |
| 34 | 3 | 1 | 1 | 1 | 4 | 1 | 1 |
| 35 | 3(2G) | 1 | 1 | 1 | 1 | 1 | 1 |
| 36 | 5 | 1 | 1 | 1 | 5 | 4(2G) | 1 |
| 37 | 4(2G) | 4(2C) | 1 | 1 | 4 | 1 | 1 |
| 38 | 1 | 1 | 1 | 1 | 4 | 1 | 1 |
| 39 | 5(2G) | 1 | 1 | 1 | 4 | 1 | 1 |
| 40 | 4(2G) | 1 | 1 | 1 | 5 | 1 | 1 |
| 41 | 4(2G) | 1 | 1 | 1 | 1 | 1 | 1 |
| 42 | 4 | 1 | 1 | 1 | 3 | 1 | 1 |
| 43 | 5 | 1 | 1 | 1 | 5 | 1 | 3 |
| 47 | 1 | 1 | 1(3G) | 1 | 1 | 1 | 1 |
| 48 | 4 | 1 | 1 | 1 | 1 | 1 | 1 |
| 49 | 1 | 1 | 1 | 1 | 1 | 1 | 1 |

TABLE 3

Soil Drench Application

| Example No. of Compound Tested | Rhizoctonia |
|---|---|
| 1 | 1 |
| 2 | 1 |
| 3 | 1 |
| 4 | 1 |
| 5 | 1 |
| 6 | 1 |
| 7 | 1 |
| 8 | 1 |
| 9 | 1 |
| 10 | 3 |
| 11 | 1 |
| 12 | 1 |
| 13 | 1 |
| 14 | 1 |
| 15 | 1 |
| 16 | 1 |
| 17 | 1 |
| 18 | 1 |
| 19 | 1 |
| 20 | 1 |
| 24 | 1 |
| 25 | 1 |
| 26 | 1 |
| 29 | 1 |
| 30 | 1 |
| 31 | 1 |
| 32 | 1 |
| 33 | 1 |
| 34 | 1 |
| 35 | 1 |
| 36 | 1 |
| 37 | 1 |
| 38 | 1 |
| 39 | 1 |
| 40 | 1 |
| 41 | 1 |
| 42 | 1 |
| 43 | 1 |
| 47 | 1 |
| 48 | 1 |
| 49 | 1 |

EXPERIMENT 3

Compounds tested in this plant disease foliage screen were formulated in the same manner as described above for Experiment 2. The 400 ppm. concentration obtained by this procedure was then serially diluted with water to obtain solutions having a lower concentration of test compound. The formulations were sprayed on the plants in the same manner as described above for foliar application. One day after treatment, the host plants were inoculated with the pathogen spores. The diseases and their corresponding host plants that were used in this experiment are as follows:

Powdery mildew—Bean
Late blight—Tomato
Apple Scab—Apple
Anthracnose—Cucumber
Rice blast—Rice
Downy mildew—Grape
Cercospora leafspot—Sugar Beet After a suitable incubation period, when disease symptoms appeared on untreated control plants, treatments were rated for disease severity according to the rating system described above. The results are recorded in Table 4.

TABLE 4

| Example No. of Compound Tested | Concentration ppm | Powdery Mildew | Late Blight | Apple Scab | Anthracnose | Rice Blast | Downy Mildew | Cercospora |
|---|---|---|---|---|---|---|---|---|
| 1 | 400 | 3 | 1 | | 1 | 1 | 1 | 3 |
| 2 | 400 | 5 | 4 | | 1 | 1 | 4 | 4 |
|   | 400 | 5 | 4 (2C) | 1 | | 5 | | 4 |
|   | 100 | 4 | 3 | 1 | | 1 | | 3 |
|   | 25 | 1 | 3 | 1 | | 1 | | 1 |
| 3 | 400 | 1 | 1 | 3 | 1 | 1 (2G) | 4 | 1 |
|   | 100 | | | | | | 4 | |
|   | 25 | | | | | | | |
| 4 | 400 | 5 | 1 | 3 | 1 | 1 | 5 | 5 |
|   | 400 | 4 | | 3 | | | 3 | 4 |
|   | 100 | 3 | | 1 | | | 3 | 3 |
|   | 25 | 1 | | 1 | | | 1 | 1 |
| 5 | 400 | 1 | 1 | | 1 | 1 | 1 | 1 |
| 6 | 400 | 4 | 1 | 5 | 1 | 1 | 4 | 1 |
|   | 400 | 1 | | | | | 1 | |
|   | 100 | 1 | | | | | | |
|   | 25 | 1 | | | | | | |
| 7 | 400 | 5 | 1 | 3 | 1 | 4 | 4 | 5 |
|   | 400 | 5 | | 1 | | 4 | 1 | 5 |
|   | 100 | 5 | | 1 | | 3 | 1 | 4 |
|   | 100 | 5 (2G) | | 1 | | 1 | 1 | 3 |
|   | 25 | 5 (2G) | | 1 | | 1 | 1 | 3 |
|   | 25 | 4 | | | | | | 1 |
|   | 6 | 1 | | | | | | 1 |
| 8 | 400 | 5 | 1 | 5 | 1 | 1 | 1 | 5 (2FS) |
|   | 400 | 5 | | | | | | 5 |
|   | 100 | 5 | | | | | | 5 |
|   | 25 | 5 | | | | | | 5 |
| 9 | 400 | 1 | 1 | 1 | 1 | 1 | 5 | 1 |
|   | 400 | | | | | | 4 | |
|   | 100 | | | | | | 5 | |
|   | 100 | | | | | | 1 | |
|   | 25 | | | | | | 5 | |
|   | 25 | | | | | | 1 | |
|   | 6 | | | | | | 1 | |
| 10 | 400 | 5 | 1 | 1 | 1 | 1 | 1 | 5 |
|   | 400 | 5 | | | | | | 4 |
|   | 100 | 5 | | | | | | 5 |
|   | 100 | 5 | | | | | | 4 |
|   | 25 | 4 | | | | | | 4 |
|   | 25 | 3 | | | | | | 1 |
|   | 6 | 1 | | | | | | 4 |
| 11 | 400 | 1 | 4 | 1 | 1 | 4 | 1 | 1 |
|   | 400 | | 3 | | | 1 | | |
|   | 100 | | 3 | | | 1 | | |
|   | 25 | | 3 | | | 1 | | |
| 12 | 400 | 1 | 1 | 1 | 1 | 1 | 1 | 1 |
| 13 | 400 | 5 | 1 | 1 | 1 | 1 | 1 | 1 |
|   | 400 | 5 | | | | | | |
|   | 100 | 4 | | | | | | |
|   | 100 | 5 | | | | | | |
|   | 25 | 4 | | | | | | |
|   | 6 | 1 | | | | | | |
| 14 | 400 | 5 | 1 | 5 (2G) | 3 | 1 | 1 | 5 |
|   | 400 | 5 | | 1 | | | | 4 |
|   | 100 | 5 | | 1 | | | | 3 |
|   | 100 | 5 | | | | | | |
|   | 25 | 4 | | 1 | | | | 1 |
|   | 25 | 4 | | | | | | |
|   | 6 | 1 | | | | | | |
| 15 | 400 | 4 | 4 | 4 | 1 | 4 | 1 | 4 |
|   | 400 | 3 | 1 | 3 | | 1 | | 1 |
|   | 100 | 1 | 1 | 1 | | 1 | | 1 |
|   | 25 | 1 | 1 | 1 | | 1 | | 1 |
| 17 | 400 | 4 | 1 | 5 | 1 | 1 | 1 | 1 (2G) |
|   | 400 | 4 | | 1 | | | | |
|   | 100 | 3 | | 1 | | | | |
|   | 25 | 1 | | 1 | | | | |
| 18 | 400 | 4 (2G) | 1 | | 1 | 1 | 1 | 5 |

TABLE 4-continued

| Example No. of Compound Tested | Concentration ppm | Powdery Mildew | Late Blight | Apple Scab | Anthracnose | Rice Blast | Downy Mildew | Cercospora |
|---|---|---|---|---|---|---|---|---|
| | 400 | 4 (2G) | | | | | | 4 |
| | 100 | 1 | | | | | | 1 |
| | 25 | 1 | | | | | | 1 |
| 19 | 400 | 4 | 1 | | 1 | 1 | 1 | 4 |
| | 400 | 5 (2G) | 3 | | | | | 4 |
| | 100 | 5 (2G) | 1 | | | | | 4 |
| | 25 | 3 | 1 | | | | | 1 |
| 20 | 400 | 4 | 3 | 5 | 1 | 1 | 1 | 1 |
| | 400 | 4 | | 3 | | | | |
| | 100 | 3 | | 1 | | | | |
| | 25 | 1 | | 1 | | | | |
| 24 | 400 | 1 | 1 | | 1 | 1 | 1 | 1 |
| 25 | 400 | 5 (2G) | 1 | 1 | 1 (2G) | 1 | 1 | 1 |
| 27 | 400 | 4 | 1 | | 3 | 1 | 1 | 4 |
| | 400 | 4 | | 4 | | | | 4 |
| | 100 | 3 | | 4 | | | | 4 |
| | 25 | 1 | | 1 | | | | 1 |
| 29 | 400 | 1 | 4 | 4 | 1 | 1 | 1 | 1 |
| | 400 | | 1 | 3 | | | | |
| | 100 | | 1 | 3 | | | | |
| | 25 | | 1 | 3 | | | | |
| 30 | 400 | 3 | 1 | | 1 | 1 | 1 | 1 |
| 33 | 400 | 3 | 3 | 1 | 1 | 1 | 1 (2G) | 1 |
| | 100 | 1 | 1 | 1 | 1 | 1 | 1 | 1 |
| | 25 | 1 | 1 | 1 | 1 | 1 | 1 | 1 |
| 37 | 400 | 5 | 1 | 5 | 1 | 1 | 1 | 5 |
| | 400 | 5 | | 3 | | | | 5 |
| | 100 | 5 | | 1 | | | | 3 |
| | 100 | 4 | | | | | | 4 |
| | 25 | 4 | | 1 | | | | 3 |
| | 25 | 1 | | | | | | 1 |
| | 6 | 3 | | | | | | 1 |
| 40 | 400 | 5 | 4 | 1 | 1 | 1 | 1 | 4 |
| | 400 | 4 (3C) | 1 | | | | | 3 |
| | 100 | 5 | 1 | | | | | 1 |
| | 100 | 4 | — | | | | | — |
| | 25 | 5 | 1 | | | | | 1 |
| | 25 | 4 | | | | | | |
| | 6 | 5 | | | | | | |
| 41 | 400 | 5 (2C) | 4 | 1 | 3 | 1 | 1 | 1 |
| | 400 | 5 (2C) | 4 | | | | | |
| | 100 | 5 | 3 | | | | | |
| | 100 | 1 | — | | | | | |
| | 25 | 5 | 3 | | | | | |
| | 25 | 1 | | | | | | |
| | 6 | 1 | | | | | | |
| 42 | 400 | 5 | 1 | 1 | 1 | 1 | 1 | 1 |
| | 400 | 5 | | | | | | |
| | 100 | 4 | | | | | | |
| | 100 | 3 | | | | | | |
| | 25 | 4 | | | | | | |
| | 25 | 1 | | | | | | |
| | 6 | 1 | | | | | | |
| 43 | 400 | 5 | 1 | 1 | 1 | 1 | 1 | 5 |
| | 400 | 4 | | | | | | 4 |
| | 100 | 4 | | | | | | 1 |
| | 25 | 1 | | | | | | 1 |
| 46 | 400 | 5 | 1 | 1 | 1 | 1 | 1 | 1 |
| | 400 | 5 | | | | | | |
| | 100 | 5 | | | | | | |
| | 100 | 3 | | | | | | |
| | 25 | 5 | | | | | | |
| | 25 | 1 | | | | | | |
| | 6 | 1 | | | | | | |
| 47 | 400 | 3 | 1 | 1 | 1 | 1 | 1 | 1 |

EXPERIMENT 4

Certain of the compounds provided by this invention were tested in an effort to evaluate their fungicidal efficacy and systemic control of various cereal grain diseases. The compounds tested were formulated as above and applied by both foliar spray and soil drench methods. The diseases and host plants employed in this test were as follows.

Powdery mildew—Wheat
Leaf rust—Wheat
Helminthosporium leaf spot—Wheat
Septoria leaf blotch—Wheat After a suitable incubation period when disease symptoms had appeared on untreated plants, treatments were rated for disease severity. The compounds were rated as above, and the results of the foliar test appear in Table 5, while the results of the soil drench test are presented in Table 6.

TABLE 5

Foliar Application

| Example No. of Compound Tested | Concentration ppm | Powdery Mildew | Leaf Rust | Helminthosporium | Septoria |
|---|---|---|---|---|---|
| 1 | 400 | 3 | 1 | 4 | 1 |
| 2 | 400 | 4 | 1 | 5 | 5 |
|   | 400 | 5 (2G) |   | 5 | 5 |
|   | 100 | 4 |   | 4 | 5 |
|   | 100 |   |   |   | 1 |
|   | 25 | 3 |   | 1 | 5 |
|   | 25 |   |   |   | 1 |
|   | 6 |   |   |   | 1 |
| 3 | 400 | 1 | 1 | 1 | 1 |
| 4 | 400 | 4 | 1 | 4 | 1 |
|   | 400 | 1 |   | 1 |   |
|   | 100 | 1 |   | 1 |   |
|   | 25 | 1 |   | 1 |   |
| 5 | 400 | 1 | 1 | 1 | 1 |
| 6 | 400 | 1 | 1 | 1 | 1 |
| 7 | 400 | 1 | 1 | 5 | 5 |
|   | 400 |   |   | 4 | 4 |
|   | 100 |   |   | 3 | 1 |
|   | 25 |   |   | 1 | 1 |
| 8 | 400 | 4 | 4 | 5 | 5 |
|   | 400 | 1 | 3 | 5 | 4 |
|   | 100 | 3 | 1 | 4 | 5 |
|   | 100 |   |   | 5 | 5 |
|   | 25 | 1 | 1 | 4 | 5 |
|   | 25 |   |   | 3 | 5 |
|   | 6 |   |   | 3 | 3 |
| 9 | 400 | 1 | 1 | 1 | 1 |
| 10 | 400 | 1 | 1 | 5 | 5 |
|   | 400 |   |   | 5 | 5 (3S) |
|   | 100 |   |   | 4 | 5 (2S) |
|   | 100 |   |   | 4 | 4 (2S) |
|   | 25 |   |   | 3 | 3 |
|   | 25 |   |   | 3 | 1 |
|   | 6 |   |   | 1 | 1 |
| 11 | 400 | 1 | 1 | 1 | 1 |
| 13 | 400 | 4 | 1 | 5 | 4 |
|   | 400 | 4 (2G) | 1 | 3 | 4 |
|   | 400 | 3 |   | 5 | 5 |
|   | 400 | 1 |   | 4 | 4 |
|   | 100 | 4 |   | 3 | 5 |
|   | 100 | 3 |   | 4 | 4 |
|   | 100 |   |   | 3 | 4 |
|   | 25 | 1 |   | 3 | 3 |
|   | 25 | 4 |   | 1 | 3 |
|   | 25 | 3 |   |   |   |
|   | 6 | 3 |   | 3 | 1 |
|   | 6 |   |   |   | 4 |
| 14 | 400 | 4 | 3 | 5 | 5 |
|   | 400 | 4 | 1 | 5 | 4 |
|   | 400 | 1 |   | 4 | 4 |
|   | 100 | 1 |   | 5 | 3 |
|   | 100 |   |   | 5 |   |
|   | 25 | 1 |   | 4 | 1 |
|   | 25 |   |   | 4 |   |
|   | 6 |   |   | 1 |   |
| 15 | 400 | 1 | 1 | 4 | 4 |
|   | 400 | 1 |   | 4 | 4 |
|   | 100 | 1 |   | 3 | 1 |
|   | 25 | 1 |   | 1 | 1 |
| 16 | 400 | 1 | 1 | 5 | 4 (2G) |
|   | 400 | 4 |   | 5 | 4 (2G) |
|   | 100 | 5 (2G) |   | 5 | 4 |
|   | 100 | 4 |   | 5 | 5 |
|   | 25 | 3 |   | 4 (2C) | 4 |
|   | 25 | 4 |   | 4 | 4 |
|   | 6 | 3 |   | 1 | 3 |
| 17 | 400 | 4 | 1 | 1 | 4 |
| 18 | 400 | 4 | 3 | 4 | 5 |
|   | 400 | 4 (2S) |   | 5 | 5 |
|   | 100 | 4 |   | 4 | 5 |
|   | 25 | 3 |   | 1 | 4 |
| 19 | 400 | 4 | 1 | 5 | 5 (2G) |
|   | 400 | 5 (2G) |   | 4 | 5 (2G) |
|   | 100 | 5 |   | 3 | 5 |
|   | 25 | 4 |   | 1 | 5 |
| 20 | 400 | 1 | 3 | 4 | 5 |
|   | 400 |   |   | 4 | 4 |
|   | 100 |   |   | 3 | 1 |
|   | 25 |   |   | 1 | 1 |
| 24 | 400 | 4 | 1 | 4 | 4 |
| 25 | 400 | 1 | 1 | 1 | 1 |
| 26 | 400 | 1 | 1 (2G) | 5 | 5 |
|   | 400 |   |   | 5 | 5 (2G) |
|   | 100 |   |   | 4 | 5 (2G) |
|   | 25 |   |   | 4 | 4 |
| 27 | 400 | 5 | 1 | 4 | 5 |
| 28 | 400 | 5 | 1 | 4 | 4 |
| 29 | 400 | 1 | 3 | 1 | 1 |
| 30 | 400 | 4 | 1 | 1 | 5 |
|   | 400 | 4 |   |   | 5 |
|   | 100 | 4 |   |   | 4 |
|   | 25 | 4 |   |   | 1 |
| 32 | 400 | 4 | 1 | 5 | 4 |
|   | 400 | 1 |   | 4 | 4 |
|   | 100 | 1 |   | 1 | 3 |
|   | 25 | 1 |   | 1 | 1 |
| 33 | 400 | 1 | 1 | 1 | 1 |
| 34 | 400 | 3 | 1 | 3 | 4 |
|   | 400 |   |   |   | 1 |
|   | 100 |   |   |   | 1 |
|   | 25 |   |   |   | 1 |
| 35 | 400 | 1 | 1 | 1 | 1 |
| 37 | 400 | 5 | 1 | 5 | 5 |
|   | 400 | 5 |   | 5 | 4 (2G) |
|   | 100 | 1 |   | 5 | 5 |
|   | 100 | 4 |   | 5 | 5 |
|   | 25 | 1 |   | 5 | 5 |
|   | 25 | 1 |   | 5 | 5 |
|   | 6 | 1 |   | 4 | 4 |
| 38 | 400 | 3 | 1 | 5 | 4 |
|   | 400 | 1 |   | 5 | 4 |
|   | 100 | 1 |   | 3 | 1 |
|   | 25 | 1 |   | 1 | 1 |
| 39 | 400 | 5 (2C) | 1 | 4 (3G) | 5 (2C) |
|   | 400 | 1 |   | 4 | 4 (2C) |
|   | 100 | 1 |   | 3 | 1 |
|   | 25 | 1 |   | 1 | 1 |
| 40 | 400 | 4 (2C) | 3 | 5 | 5 |
|   | 400 | 4 (2C) |   | 4 | 4 |
|   | 100 | 1 |   | 5 | 4 |
|   | 100 |   |   | 4 | 4 |
|   | 25 | 1 |   | 4 | 3 |
|   | 25 |   |   | 4 | 1 |
|   | 6 |   |   | 1 | 3 |
| 41 | 400 | 4 (3G) | 1 | 4 (3G) | 4 (2G) |
|   | 400 | 1 |   | 4 | 4 |
|   | 100 | 1 |   | 1 | 1 |
|   | 25 | 1 |   | 1 | 1 |
| 42 | 400 | 4 | 1 | 5 | 4 (2G) |
|   | 400 | 3 |   | 4 | 4 |
|   | 100 | 1 |   | 3 | 3 |
|   | 25 | 1 |   | 1 | 1 |
| 43 | 400 | 4 | 1 | 4 (2C) | 5 |
|   | 400 | 4 |   | 4 | 4 (2G) |
|   | 100 | 4 |   | 4 | 5 |
|   | 25 | 1 |   | 1 | 3 |
| 46 | 400 | 5 | 1 | 5 | 4 |
|   | 400 | 1 |   | 5 | 4 |
|   | 100 | 1 |   | 4 | 1 |
|   | 25 |   |   | 1 | 1 |
| 48 | 400 | 1 | 1 | 4 | 1 |
|   | 400 |   |   | 1 |   |
|   | 100 |   |   | 1 |   |
|   | 25 |   |   | 1 |   |

TABLE 6

Soil Drench Application

| Example No. of Compound Tested | Concentration lbs./acre (kg./ha.) | Powdery Mildew | Leaf Rust | Helminthosporium | Septoria |
|---|---|---|---|---|---|
| 1 | 11.0(12.3) | 1 | 1 | 1 | 1 |
| 2 | 11.0(12.3) | 4 | 1 | 1 | 4 |
|   | 11.0(12.3) | 3 |   |   | 4 |
|   | 3.0(3.36) | 1 |   | 1 |   |
|   | 0.7(0.78) | 1 |   |   | 1 |
| 3 | 11.0(12.3) | 1 | 1 | 1 | 1 |
| 4 | 11.0(12.3) | 1 | 1 | 1 | 1 |
| 5 | 11.0(12.3) | 1 | 1 | 1 | 1 |
| 6 | 11.0(12.3) | 1 | 1 | 1 | 1 |
| 7 | 11.0(12.3) | 5 (2C) | 4 (2G) | 1 | 4 |
|   | 11.0(12.3) | 5 (2C) | 1 |   | 5 |
|   | 3.0(3.36) | 1 | 1 |   | 1 |
|   | 0.7(0.78) | 1 | 1 |   | 1 |
| 8 | 11.0(12.3) | 4 | 1 | 1 | 1 |
|   | 11.0(12.3) | 4 |   |   | 3 |
|   | 3.0(3.36) | 3 |   |   | 1 |
|   | 0.7(0.78) | 1 |   |   | 1 |
| 9 | 11.0(12.3) | 1 | 1 | 1 | 1 |
| 10 | 11.0(12.3) | 1 | 1 | 1 | 4 |
|   | 11.0(12.3) |   |   |   | 3 |
|   | 3.0(3.36) |   |   |   | 1 |
| 11 | 11.0(12.3) | 1 | 1 | 1 | 1 |
| 13 | 11.0(12.3) | 5 | 1 | 1 | 4 |
|   | 11.0(12.3) | 4 | 1 | 4 | 1 |
|   | 11.0(12.3) | 4 |   | 1 | 4 |
|   | 11.0(12.3) | 5 |   |   | 4 |
|   | 3.0(3.36) | 1 |   | 1 | 1 |
|   | 3.0(3.36) | 1 |   | 1 | 1 |
|   | 0.7(0.78) | 1 |   | 1 | 1 |
|   | 0.7(0.78) | 1 |   | 1 |   |
|   | 0.2(0.22) |   |   | 1 |   |
| 14 | 11.0(12.3) | 4 (2C) | 1 | 1 | 4 |
|   | 11.0(12.3) | 5 | 1 | 1 | 1 |
|   | 11.0(12.3) | 4 |   |   |   |
|   | 3.0(3.36) | 3 |   |   |   |
|   | 0.7(0.78) | 1 |   |   |   |
| 15 | 11.0(12.3) | 4 | 1 | 1 | 1 |
|   | 11.0(12.3) | 4 |   |   |   |
|   | 3.0(3.36) | 1 |   |   |   |
|   | 0.7(0.78) |   |   |   |   |
| 16 | 11.0(12.3) | 5 | 1 | 1 | 4 |
|   | 11.0(12.3) | 5 |   |   | 4 |
|   | 3.0(3.36) | 3 |   |   | 4 |
|   | 3.0(3.36) | 1 |   |   | 1 |
|   | 0.7(0.78) | 1 |   |   | 3 |
|   | 0.7(0.78) | 1 |   |   | 1 |
|   | 0.2(0.22) | 1 |   |   | 1 |
| 17 | 11.0(12.3) | 1 | 1 | 1 | 1 |
| 18 | 11.0(12.3) | 4 | 1 | 1 | 5 |
|   | 11.0(12.3) | 1 |   |   | 1 |
|   | 3.0(3.36) | 1 |   |   | 1 |
|   | 0.7(0.78) | 1 |   |   | 1 |
| 19 | 11.0(12.3) | 4 | 1 | 1 | 3 (2G) |
|   | 11.0(12.3) | 1 |   |   | 4 (2G) |
|   | 3.0(3.36) | 1 |   |   | 1 |
|   | 0.7(0.78) | 1 |   |   | 1 |
| 20 | 11.0(12.3) | 1 | 1 | 1 | 4 |
|   | 11.0(12.3) | 1 |   |   | 1 |
|   | 3.0(3.36) | 1 |   |   | 1 |
|   | 0.7(0.78) | 1 |   |   | 1 |
| 24 | 11.0(12.3) | 4 | 1 | 1 | 4 |
| 25 | 11.0(12.3) | 1 | 1 (2G) | 1 | 1 |
| 26 | 11.0(12.3) | 1 | 1 | 1 | 1 |
| 27 | 11.0(12.3) | 5 | 1 | 1 | 4 (2G) |
| 28 | 11.0(12.3) | 1 | 1 | 4 | 1 |
| 29 | 11.0(12.3) | 1 | 1 | 1 | 1 |
| 30 | 11.0(12.3) | 5 | 1 | 1 | 4 |
|   | 11.0(12.3) | 4 |   |   | 4 |
|   | 3.0(3.36) | 1 |   |   | 4 |
|   | 0.7(0.78) | 1 |   |   | 1 |
| 32 | 11.0(12.3) | 3 | 1 | 1 | 1 |
| 33 | 11.0(12.3) | 1 | 1 | 1 | 1 |
| 34 | 11.0(12.3) | 1 | 1 |   |   |
| 35 | 11.0(12.3) | 4 (2C) | 1 |   |   |
| 37 | 11.0(12.3) | 1 | 1 |   | 1 (2S) |
|   | 11.0(12.3) | 4 |   | 1 (2S) | 5 |
|   |   |   |   |   | 5 (2C) |
|   | 3.0(3.36) | 3 |   |   | 3 |
|   | 0.7(0.78) | 1 |   |   | 1 |
| 38 | 11.0(12.3) | 4 | 1 | 1 | 4 (2S) |
|   | 11.0(12.3) | 4 |   |   | 1 (2G) |
|   | 3.0(3.36) | 1 |   |   | 1 |
|   | 0.7(0.78) | 1 |   |   | 1 |
| 39 | 11.0(12.3) | 4 (2C) | 1 | 1 | 1 (2C) |
|   | 11.0(12.3) | 1 |   |   |   |
|   | 3.0(3.36) | 1 |   |   |   |
|   | 0.7(0.78) |   |   |   |   |
| 40 | 11.0(12.3) | 4 | 1 | 1 | 1 |
|   | 11.0(12.3) | 4 |   |   |   |
|   | 3.0(3.36) | 1 |   |   |   |
|   | 0.7(0.78) | 1 |   |   |   |
| 41 | 11.0(12.3) | 1 | 1 | 1 | 1 (2G) |
| 42 | 11.0(12.3) | 4 | 1 | 1 | 1 |
|   | 11.0(12.3) | 1 |   |   |   |
|   | 3.0(3.36) | 1 |   |   |   |
|   | 0.7(0.78) | 1 |   |   |   |
| 43 | 11.0(12.3) | 5 | 1 | 1 | 1 (2G) |
|   | 11.0(12.3) | 4 |   |   |   |
|   | 3.0(3.36) | 3 |   |   |   |
| 46 | 11.0(12.3) | 1 | 1 | 3 | 4 |
|   | 11.0(12.3) |   |   |   | 4 |
|   | 3.0(3.36) |   |   |   | 1 |
|   | 0.7(0.78) |   |   |   | 1 |
| 48 | 11.0(12.3) | 1 | 1 | 1 | 1 |

EXPERIMENT 5

Certain compounds of this invention have additionally been evaluated in soil disease tests to demonstrate their antifungal activity. Test compounds were formulated by dissolving 57 mg. of compound in 1 ml. of a fifty percent (v/v) solution of acetone and ethanol. A 0.1% aqueous solution of Tween 20 was added to bring the final volume to 16 ml.

Pathogen-infested soil was placed in 8 oz. paper cups. A depression was made in the surface of the soil and 3 g. of Celatom MP-78 granules were placed in the depression. A 4 ml. aliquot of chemical formulation, equivalent to a rate of 40 lbs./acre (44.8 kg./ha.), was added to the granules, and the cups were then covered with lids. The containers were shaken by hand for about 10 seconds, and then placed on a roller for about 10 minutes to thoroughly incorporate the test chemical into the soil. The treated soil was transferred to a 2.5 inch round plastic pot, and seeds of the host plant were added, and covered with additional treated soil. The pathogens and their host plants were as follows:

Rhizoctonia—Cotton
Pythium—Cotton
Fusarium—Bean
Verticillium—Cotton

The effect of the test compounds was observed on the growing plants and was rated on a scale of 1 to 5 (1 is severe disease, 5 is no disease). The results of such evaluations are presented in Table 7.

TABLE 7

| Example No. of Compound Tested | Rhizoctonia | Pythium | Fusarium | Verticillium |
|---|---|---|---|---|
| 1 | 1 | 1 | 1 | 1 |
| 3 | 1 | 1 | 1 | 1 |
| 6 | 1 | 1 | 1 | 1 |
| 7 | 1 | 1 | 4 | 1 |

TABLE 7-continued

| Example No. of Compound Tested | Rhizoctonia | Pythium | Fusarium | Verticillium |
|---|---|---|---|---|
| 8 | 3 | 1 | 4 | 1 |
| 9 | | | | 1 |
| 10 | 1 | 1 | 3 | 5 |
| 11 | 1 | 3 | 1 | 1 |
| 36 | 5 | 1 | 5 | 1 |
| 42 | 1 | 1 | 1 | 1 |

EXPERIMENT 6

A number of compounds of the present invention were also tested to evaluate their ability to control fungal diseases that commonly infest turfgrasses.

The compound was dissolved in a solution containing 1000 ppm. each of the surfactants Toximul R and S combined with a mixture of ethanol and acetone in a 1:1 ratio. This solution was then serially diluted with water to provide sprayable formulations for application rates of 0.5, 1, 2 and 4 pounds of active ingredient per acre (0.56, 1.12, 2.24 and 4.48 kg./ha. respectively). Additional dilution with water provided lower test compound concentrations. Each formulated test compound was tested against four different fungal diseases. Each compound was foliar applied to Penncross creeping bentgrass (*Agrostis palustris*) which was then artificially inoculated with Rhizoctonia spawn (*Rhizoctonia solani*), Fusarium spawn (*Fusarium roseum*), and dollarspot spawn (*Sclerotinia homoeocarpa*), in separate pots. The formulated compound was also foliar applied to common Kentucky bluegrass (*Poa pratensis*) prior to the grass being artificially inoculated with a spore suspension of *Helminthosporium sativum*. Pennfine perennial ryegrass (*Lolium perenne*) was treated with a test compound prior to being inoculated with *Pythium aphanidermatum*. All of the individually treated, inoculated turf pots were incubated at 27° C. in a climate having greater than 90% relative humidity. The treatments were then visually evaluated 7 and 14 days following treatment for disease severity and turfgrass tolerance according to the following scales:

| Disease Severity | Turfgrass Tolerance |
|---|---|
| 5 = no disease | 1 = no injury |
| 4 = slight disease | 2 = slight injury |
| 3 = moderate disease | 3 = moderate injury |
| 2 = severe disease | 4 = severe injury |
| 1 = 100% of plant tissue is infected | 5 = death of turf |

The results of this experiment appear below in Table 8. The numbers in parentheses refer to turfgrass tolerance ratings and where no value is recorded, there was no injury observed.

TABLE 8

| Example No. of Compound Tested | Application Rate lbs./acre (kg./ha.) | 7 Days | | | | | 14 Days | | | | |
|---|---|---|---|---|---|---|---|---|---|---|---|
| | | Helmintho-sporium | Pythium | Rhizoc-tonia | Sclero-tinia | Fusarium | Helmintho-sporium | Pythium | Rhizoc-tonia | Sclero-tinia | Fusarium |
| 1 | 0.125(0.14) | 1 | | 1 | 2 | | 1 | | 1 | 4 | |
| | 0.25 (0.28) | 1 | | 1 | 3 | | 1 | | 1 | 4.5 | |
| | 0.50 (0.56) | 2 | | 1 | 3(2) | | 2 | | 1 | 4.5 | |
| | 1.0 (1.12) | 3 | | 2.5 | 3(3) | | 3 | | 3 | 4.5 | |
| 2 | 0.5 (0.56) | 4 | 1 | 3 | 4 | 4 | 4 | | 2 | 4 | 4 |
| | 1.0 (1.12) | 4 | 1 | 3 | 4 | 4 | 4 | 2 | 2 | 4 | 3 |
| | 2.0 (2.24) | 4.5 | 2 | 3 | 4 | 4 | 4 | 3 | 2 | 4 | 3 |
| | 4.0 (4.48) | 5 | 3 | 3 | 4 | 4 | 4 | 3 | 2 | 4(2) | 3 |
| 4 | 0.125(0.14) | 1 | | | | | 1 | | | | |
| | 0.25 (0.28) | 2 | | | | | 2.5 | | | | |
| | 0.50 (0.56) | 3 | | | | | 3.5 | | | | |
| | 1.0 (1.12) | 4 | | | | | 4 | | | | |
| 5 | 0.5 (0.56) | 2 | 1 | 1 | 3 | 1 | 2 | 1 | 1 | 3 | 1 |
| | 1.0 (1.12) | 2 | 1 | 1 | 3 | 1 | 2 | 1 | 1 | 3 | 1 |
| | 2.0 (2.24) | 2 | 2 | 1 | 3 | 1 | 3 | 2 | 1 | 3 | 1 |
| | 4.0 (4.48) | 2 | 3 | 1 | 3 | 1 | 2 | 3 | 1 | 3 | 1 |
| 7 | 0.125(0.14) | 2 | | 2 | 4 | | 2 | | 3 | 4.5 | |
| | 0.25 (0.28) | 3 | | 2.5 | 4 | | 3 | | 3 | 5 | |
| | 0.50 (0.56) | 4 | | 1 | 4(2) | | 3.5 | | 1 | 5 | |
| | 1.0 (1.12) | 4 | | 3.5 | 4(2) | | 4 | | 4 | 5 | |
| 8 | 0.125(0.14) | 3.5 | | 4 | 3 | | 3 | | 4 | 4.5 | |
| | 0.25 (0.28) | 4 | | 4 | 3 | | 4 | | 5 | 5 | |
| | 0.50 (0.56) | 5 | | 4(2) | 3 | | 4.5 | | 4.5 | 5 | |
| | 1.0 (1.12) | 5 | | 4(3) | 3(2) | | 4.5 | | 4.5(2) | 5 | |
| 16 | 0.125(0.14) | 3 | | 3 | 4 | | 3 | | 4 | 4 | |
| | 0.25 (0.28) | 4 | | 3.5 | 4 | | 4 | | 4 | 4 | |
| | 0.50 (0.56) | 5 | | 4 | 4 | | 4.5 | | 4.5 | 4 | |
| | 1.0 (1.12) | 5 | | 4(2) | 4(2) | | 5 | | 4.5 | 4 | |
| 17 | 0.5 (0.56) | 1 | 1 | 1 | 1 | 1 | 1 | 1 | 1 | 1 | 1 |
| | 1.0 (1.12) | 1 | 1 | 1 | 1 | 3 | 1 | 1 | 1 | 1 | 1 |
| | 2.0 (2.24) | 1 | 1 | 1 | 1 | 3 | 2 | 2 | 1 | 1 | 2 |
| | 4.0 (4.48) | 3 | 2 | 1 | 1 | 4 | 2 | 2 | 1 | 1 | 2 |
| 18 | 0.5 (0.56) | 2 | 1 | 2 | 1 | 1 | 2 | 1 | 2 | 1 | 1 |
| | 1.0 (1.12) | 3 | 1 | 2 | 1 | 3 | 2 | 1 | 2 | 1 | 1 |
| | 2.0 (2.24) | 4 | 1 | 2 | 1 | 3 | 3.5 | 1 | 3 | 1 | 1 |
| | 4.0 (4.48) | 5 | 1 | 3 | 1 | 3 | 4.5 | 1 | 3 | 1 | 1 |
| 19 | 0.5 (0.56) | 3.5 | 1 | 1 | 3 | 3 | 3.5 | 1 | 1 | 3 | 1 |
| | 1.0 (1.12) | 4 | 1 | 1 | 3 | 3 | 4 | 2 | 1 | 3 | 1 |
| | 2.0 (2.24) | 5 | 3 | 1 | 3 | 3 | 5 | 3 | 1 | 4 | 2 |
| | 4.0 (4.48) | 5 | 4 | 1 | 3.5 | 3 | 4.5 | 2 | 1 | 4 | 2 |
| 21 | 0.125(0.14) | 2 | | 1 | 3 | | 1 | | 1 | 4 | |
| | 0.25 (0.28) | 3 | | 1 | 3 | | 3 | | 1 | 4 | |
| | 0.50 (0.56) | 4 | | 2 | 3 | | 3.5 | | 2 | 4 | |

TABLE 8-continued

| Example No. of Compound Tested | Application Rate lbs./acre (kg./ha.) | 7 Days | | | | | 14 Days | | | | |
|---|---|---|---|---|---|---|---|---|---|---|---|
| | | Helmintho-sporium | Pythium | Rhizoc-tonia | Sclero-tinia | Fusarium | Helmintho-sporium | Pythium | Rhizoc-tonia | Sclero-tinia | Fusarium |
| | 0.5 (0.56) | 5 | 1 | 1 | 4 | 4 | 4.5 | 1 | 1 | 4 | 4 |
| | 1.0 (1.12) | 4.5 | | 3(2) | 3(2) | | 4 | | 3(2) | 4 | |
| | 1.0 (1.12) | 5 | 1 | 1 | 5 | 4 | 5 | 1 | 1 | 5 | 3 |
| | 2.0 (2.24) | 5 | 1 | 1 | 5 | 4 | 5 | 1 | 1 | 5 | 4 |
| | 4.0 (4.48) | 5 | 2 | 1 | 4.5 | 4 | 5(2) | 1 | 1 | 5 | 4 |
| 22 | 0.5 (0.56) | 2 | 1 | 1 | 4 | 3 | 2 | 1 | 1 | 4 | 1 |
| | 1.0 (1.12) | 2 | 1 | 3 | 4 | 3 | 2 | 1 | 2 | 4 | 1 |
| | 2.0 (2.24) | 3 | 1 | 2 | 4 | 3 | 3.5 | 1 | 1 | 4.5 | 1 |
| | 4.0 (4.48) | 4 | 1 | 3 | 4.5 | 4 | 5 | 2 | 3 | 5 | 1 |
| 23 | 0.5 (0.56) | 1 | 1 | 1 | 1 | 1 | 1 | 1 | 1 | 1 | 1 |
| | 1.0 (1.12) | 1 | 1 | 1 | 1 | 1 | 1 | 1 | 1 | 1 | 1 |
| | 2.0 (2.24) | 2 | 1 | 3 | 1 | 1 | 1 | 1 | 3 | 1 | 1 |
| | 4.0 (4.48) | 3 | 1 | 3 | 1 | 2 | 3 | 1 | 3 | 1 | 1 |
| 25 | 0.5 (0.56) | 1 | 1 | 3 | | | 1 | 1 | 1 | | |
| | 1.0 (1.12) | 2 | 1 | 3 | | | 1 | 1 | 3 | | |
| | 2.0 (2.24) | 4 | 2 | 3 | | | 2 | 2 | 3 | | |
| | 4.0 (4.48) | 5 | 3 | 3 | | | 3.5 | 3 | 2 | | |
| 26 | 0.5 (0.56) | 3 | 1 | 3 | | | 3 | 1 | 3 | | |
| | 1.0 (1.12) | 4 | 2 | 3.5 | | | 3.5 | 1 | 3 | | |
| | 2.0 (2.24) | 5 | 2 | 4 | | | 4 | 1 | 4 | | |
| | 4.0 (4.48) | 5 | 4 | 4 | | | 4.5 | 3 | 4 | | |
| 27 | 0.5 (0.56) | 2 | 1 | 3 | | | 1 | 1 | 2 | | |
| | 1.0 (1.12) | 3 | 1 | 3 | | | 2 | 1 | 2 | | |
| | 2.0 (2.24) | 4 | 1 | 3.5 | | | 3.5 | 1 | 3 | | |
| | 4.0 (4.48) | 4 | 1 | 3.5 | | | 4 | 1 | 3 | | |
| 28 | 0.5 (0.56) | 3 | 2 | 1 | | | 2 | 1 | 1 | | |
| | 1.0 (1.12) | 4 | 3 | 3 | | | 2 | 1 | 1 | | |
| | 2.0 (2.24) | 4.5 | 3 | 3 | | | 2.5 | 1 | 1 | | |
| | 4.0 (4.48) | 4.5 | 3 | 3.5 | | | 3.5 | 2 | 2(2) | | |
| 30 | 0.5 (0.56) | 1 | 1 | 1 | 1 | 3 | 1 | 1 | 1 | 1 | 1 |
| | 1.0 (1.12) | 1 | 1 | 1 | 1 | 3 | 1 | 1 | 1 | 1 | 1 |
| | 2.0 (2.24) | 1 | 2 | 3 | 1 | 3 | 1 | 3 | 3 | 1(2) | 1 |
| | 4.0 (4.48) | 2 | 2 | 3 | 1 | 3 | 2.5 | 3 | 3 | 1(2) | 1 |

EXPERIMENT 7

Example 13 of the present invention, N-(4-chlorophenyl)-N-(4,5-dihydro-2-thiazolyl)-[(3-pyridyl)methyl]amine, was also tested in a field study to further evaluate the compound's ability to control certain turfgrass disease pathogens.

The compound was formulated as an emulsifiable concentrate. The formulation contained the following percentages and ingredients by weight:

| | |
|---|---|
| 48.0 | N—(4-chlorophenyl)-N—(4,5-dihydro-2-thiazolyl)-[(3-pyridyl)methyl]amine |
| 3.0 | Toximul H |
| 7.0 | Toximul D (Toximul H and D are surfactants manufactured by Stepan Chemical Company, Northfield, Illinois) |
| 20.0 | 2-Methoxyethanol |
| 22.0 | Xylenes |
| 100.0 | |

The formulation was diluted with deionized water to afford the appropriate test compound concentrations. The solution was applied to the corresponding infected turfgrasses as above described. Observations were made both 7 and 14 days following treatments and the results were recorded using the 1 to 5 rating scale as described above. The results from this test are presented below in Table 9.

TABLE 9

| Concentration lbs./acre (kg./ha.) | 7 Days | | | | | 14 Days | | | | |
|---|---|---|---|---|---|---|---|---|---|---|
| | Helmintho-sporium | Pythium | Rhizoc-tonia | Sclero-tinia | Fusarium | Helmintho-sporium | Pythium | Rhizoc-tonia | Sclero-tinia | Fusarium |
| 0.125(0.14) | 3.5 | 1 | 3 | 4 | 1 | 4 | 1 | 3.5 | 3 | 1 |
| 0.250(0.28) | 4 | 1 | 4 | 5 | 1 | 4 | 1 | 4 | 4 | 1 |
| 0.500(0.56) | 5 | 1 | 4.5 | 5 | 1 | 5 | 1 | 4.5 | 5 | 1 |
| 1.000(1.12) | 5 | 1 | 5 | 5 | 1 | 5 | 1 | 5 | 5 | 1 |
| 2.000(2.24) | 5 | 1 | 5 | 5 | 1 | 5 | 1 | 5 | 5 | 1 |

The compounds of the present invention may be formulated with a suitable agriculturally-acceptable carrier to provide yet another embodiment of the invention. Such compositions will contain from about 0.1 to about 95.0 percent by weight of the active ingredient, depending on the composition desired. Preferred formulations will contain from about 1 to about 50 percent active ingredient. Sprayable formulations are preferred primarily because of their rapidity and economy of application.

The most convenient formulations contemplated are in the form of concentrated compositions. Such formulations are diluted with water, generally at or near the site of application and are applied by spraying the resulting water dispersion or emulsion. The diluted compositions generally will contain the active ingredient in the range from about 0.1 percent to about 10 percent by weight. Water-dispersible or emulsifiable compositions may be either solids, usually known as wettable powders, or liquids, usually known as emulsifiable concentrates or aqueous suspensions.

A typical wettable powder comprises an intimate mixture of a compound of the invention, an inert carrier, and one or more surfactants. The concentration of the active compound is usually from about 5 percent to about 90 percent by weight, ideally about 25 to about 80 percent. The inert carrier is usually chosen from among the attapulgite clays, the montmorillonite clays, the diatomaceous earths, the purified silicates, or other similar substances that are readily available. Effective surfactants, comprising from about 0.5 percent to about 15 percent by weight of the wettable powder, are chosen from among the sulfonated lignins, the condensed naphthalenesulfonates, the alkyl sulfates, and related materials.

The most popular type of formulation is an emulsifiable concentrate. A typical emulsifiable concentrate comprises from about 0.1 to about 6 pounds of a compound of the invention per gallon of liquid (0.012 to 0.72 kg./l.), dissolved in a mixture of an organic solvent and an emulsifier. The organic solvent will be immiscible with water and is chosen with regard to its solvency and its cost. Examples of solvents which may be employed include the aromatics, especially the xylenes, 2-chlorotoluene, acetophenone, isophorone and heavy aromatic naphtha. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as ethoxylated alkyl phenols, ethoxylated alkyl ethers, sorbitan esters, ethoxylated alkyl alcohols, and—ethoxylated sorbitan esters and ethers, and are used at similar percentages as for wettable powders.

Dust compositions are most often prepared for fungicides and will typically contain a lower level of the active ingredient than will be present in other formulations and will be dispersed in finely divided inert carriers. Dusts generally will contain a compound of the present invention in an amount from about 0.1 to about 10 percent by weight. Dusts are prepared by intimately mixing and finely grinding the compound with an inert solid diluent or carrier such as ground montmorillonite clay, attapulgite clay, talc, ground volcanic rock, kaolin clay, or other inert, relatively dense, inexpensive substances.

Solid, granular compositions are convenient for the application of compounds of this invention to the soil. Granules comprise a compound of the invention dispersed on a granular inert carrier such as coarsely ground clay of from about 0.1 to about 3 mm. particle size. The compound is most conveniently applied to the clay by dissolving it in an inexpensive solvent such as acetone and applying the solution to the sized clay in an appropriate solids mixer. The solvent is then removed by evaporation or the like.

The following examples provide an illustration of typical agricultural compositions comprehended by this invention.

| Wettable Powder | |
|---|---|
| Ingredient | Concentration by weight (%) |
| N—(2-Methyl-4-chlorophenyl)-N—4,5-dihydro-2-thiazolyl)-[(3-pyridyl)-methyl]amine | 45.0 |
| Igepal CA-6.30, a polyoxyethylene octyl phenol nonionic wetting agent-GAF Corp. | 10.0 |
| Polyfon 0, emulsifier from Westvaco Corp. | 5.0 |
| Zeolex 7, a hydrated silicate from J. M. Huber Corp. | 5.0 |
| Barden Clay from J. M. Huber Corp. | 35.0 |
| | 100.0 |

The active ingredient is finely divided into a powder and blended to uniformity with the agronomic carriers using a hammer mill or micro mill to form a free flowing powder that will be wetted and suspendible in water at or near the site of application to form a sprayable mixture. The composition is then sprayed on the locus where control is desired. The application is done at a volume rate so that the active ingredient is present at about 1 to about 4 pounds per acre (about 1.12 to about 4.48 kg./ha.).

| Dust | |
|---|---|
| Ingredient | Concentration by weight (%) |
| N—(2-Chloro-4-methylphenyl)-N—(4,5-dihydro-2-thiazolyl)-[(3-pyridyl)-methyl]amine | 8.0 |
| Diatomite, a diatomaceous earth, Witco Chemical Corp., Inorganic Specialties Division | 92.0 |
| | 100.0 |

The active ingredient is suspended in a solvent such as acetone and sprayed onto a carrier such as diatomaceous earth. The solvent is then removed by evaporation and the dry mixture is ground to a fine powder of uniform particle size of about 10 to about 40 microns. The dust formulation can be diluted at the site of application if desired by the addition of additional excipient such as silica or clay. The dust is surface applied to the locus where control is desired, either by conventional ground equipment or aireally.

| Granules | |
|---|---|
| Ingredient | Concentration by weight (%) |
| N—(4-Phenoxyphenyl)-N—(4,5-dihydro-2-thiazolyl)-[(3-pyridyl)methyl[amine | 5.0 |
| Heavy aromatic naphtha | 5.0 |
| Florex 30/60 granular clay, The Floridian Company | |
| | 100.0 |

The active agent is dissolved in the naphtha and sprayed onto the clay granules, typically under agitation, and the formulated granules are sieved to provide a uniform mesh size.

| Aqueous Suspension | |
|---|---|
| Ingredient | Concentration by weight (%) |
| N—(2,4-Dichlorophenyl)-N—(4,5-dihydro-2-thiazolyl)-[(3-pyridyl)methyl]amine | 45.0 |
| Polyfon H, emulsifier from Westvaco Corporation | 3.0 |
| Sponto 2174, emulsifier from Witco Chemical Corporation | 4.0 |
| Ethylene Glycol | 8.0 |
| Xanthum Gum thickening agent | 0.2 |
| Antifoam C foam suppressant, from Dow Corning | 0.5 |
| Water | 39.3 |
| | 100.0 |

Typically the water and soluble components are mixed in a tank equipped with a high shear mixer. The solid active ingredient is next added and mixed. The entire mixture is then passed through a liquid grinding mill until the desired particle size is reached. The final step in the preparation of the suspension is to blend the xanthum gum to the mixture. The aqueous suspension is then typically diluted with additional water and sprayed on the application site.

We claim:

1. A compound of the formula

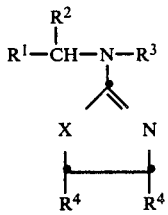

wherein
$R^1$ is

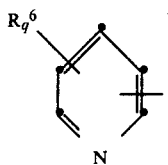

$R^2$ is hydrogen, $C_1$–$C_4$ alkyl or

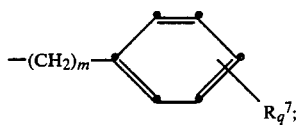

$R^3$ is $C_2$–$C_{10}$ alkenyl, $C_1$–$C_{10}$ alkoxy, $C_1$–$C_{10}$ haloalkyl, $C_1$–$C_{10}$ haloalkoxy, $C_3$–$C_8$ cycloalkyl, 1,3-benzodioxolyl or

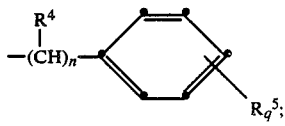

each $R^4$ is independently hydrogen or $C_1$–$C_4$ alkyl;

each $R^5$ is independently $C_1$–$C_6$ alkyl, $C_1$–$C_6$ alkoxy, $C_3$–$C_8$ cycloalkyl, $C_1$–$C_6$ alkylthio, halogen, $C_1$–$C_6$ haloalkyl, $C_1$–$C_6$ haloalkoxy, nitro, cyano or

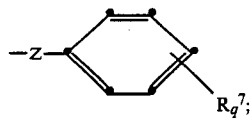

each $R^6$ is independently halogen, $C_1$–$C_4$ alkyl, $C_1$–$C_4$ haloalkyl or $C_1$–$C_4$ haloalkoxy;
each $R^7$ is independently $C_1$–$C_6$ alkyl, $C_1$–$C_6$ alkoxy, $C_3$–$C_8$ cycloalkyl, $C_1$–$C_6$ alkylthio, halogen, $C_1$–$C_6$ haloalkyl, $C_1$–$C_6$ haloalkoxy, nitro or cyano;
X is O or S;
Z is O, S, —(CH$_2$)$_n$— or a direct link;
m is 0 or 1;
each n is independently 0, 1, 2 or 3;
each q is independently 0, 1 or 2;
and the agronomically-acceptable salts thereof.

2. A compound of claim 1 wherein X is S.
3. A compound of claim 2 wherein m is 1.
4. A compound of claim 2 wherein m is 0.
5. A compound of claim 4 wherein $R^3$ is

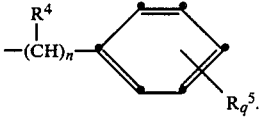

6. A compound of claim 5 wherein n is 0.
7. A compound of claim 6 wherein $R^1$ is 3-pyridyl.
8. A compound of claim 7 wherein $R^5$ is halogen.
9. The compound of claim 8 which is N-(4-chlorophenyl)-N-(4,5-dihydro-2-thiazolyl)-[(3-pyridyl)methyl]amine.
10. The compound of claim 8 which is N-(2,4-dichlorophenyl)-N-(4,5-dihydro-2-thiazolyl)-[(3-pyridyl)methyl]amine.
11. The compound of claim 8 which is N-(4-chlorophenyl)-N-(4,5-dihydro-2-thiazolyl)-[1-(3-pyridyl)ethyl]amine.
12. The compound of claim 8 which is N-(2,4-difluorophenyl)-N-(4,5-dihydro-2-thiazolyl)-[(3-pyridyl)methyl]amine.
13. The compound of claim 8 which is N-(4-chlorophenyl)-N-(4,5-dihydro-4-methyl-2-thiazolyl)-[1-(3-pyridyl)ethyl]amine.
14. A compound of claim 7 wherein each $R^5$ is independently halogen or $C_1$–$C_6$ alkyl.
15. The compound of claim 14 which is N-(2-chloro-4-methylphenyl)-N-(4,5-dihydro-2-thiazolyl)-[(3-pyridyl)methyl]amine.
16. The compound of claim 14 which is N-(2-methyl-4-chlorophenyl)-N-(4,5-dihydro-2-thiazolyl)-[(3-pyridyl)methyl]amine.
17. A compound of claim 7 wherein $R^5$ is

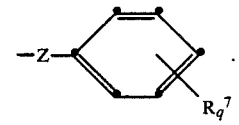

18. A compound of claim 17 wherein Z is oxygen.

19. The compound of claim 18 which is N-(4-phenoxyphenyl)-N-(4,5-dihydro-2-thiazolyl)-[(3-pyridyl)methyl]amine.

20. A method for controlling the growth of aquatic plants which comprises adding to the water containing said plants, or contacting the plants with, a growth regulating amount of a compound of claim 1.

21. A method of claim 20 wherein X is S.

22. A method of claim 21 wherein m is 0.

23. A method of claim 22 wherein $R^3$ is

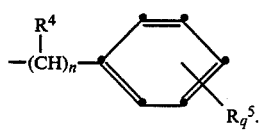

24. A method of claim 23 wherein n is 0.

25. The method of claim 24 wherein the compound is N-(4-chlorophenyl)-N-(4,5-dihydro-5-methyl-2-thiazolyl)-[(3-pyridyl)methyl]amine.

26. The method of claim 24 wherein the compound is N-(4-chlorophenyl)-N-(4,5-dihydro-4-methyl-2-thiazolyl)-[(3-pyridyl)methyl]amine.

27. The method of claim 26 wherein the compound is N-(4-chlorophenyl)-N-(4,5-dihydro-2-thiazolyl)-[(3-pyridyl)methyl]amine.

28. The method of claim 26 wherein the compound is N-(2-methyl-4-chlorophenyl)-N-(4,5-dihydro-2-thiazolyl)-[(3-pyridyl)methyl]amine.

29. A method for controlling the growth of fungal diseases which comprises applying to the locus of the plant for which control is desired a disease inhibiting and non-herbicidal amount of a compound of claim 1.

30. A method of claim 29 wherein X is S.

31. A method of claim 30 wherein m is 1.

32. A method of claim 30 wherein m is 0.

33. A method of claim 32 wherein $R^3$ is

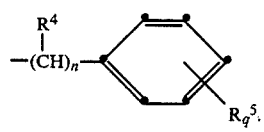

34. A method of claim 33 wherein n is 0.

35. A method of claim 34 wherein $R^1$ is 3-pyridyl.

36. A method of claim 35 wherein $R^5$ is halogen.

37. The method of claim 36 wherein the compound is N-(4-chlorophenyl)-N-(4,5-dihydro-2-thiazolyl)-[(3-pyridyl)methyl]amine.

38. The method of claim 36 wherein the compound is N-(2,4-dichlorophenyl)-N-(4,5-dihydro-2-thiazolyl)-[(3-pyridyl)methyl]amine.

39. The method of claim 38 wherein the compound is N-(4-chlorophenyl)-N-(4,5-dihydro-2-thiazolyl)-[1-(3-pyridyl)ethyl]amine.

40. A method of claim 37 wherein $R^5$ is halogen or $C_1$–$C_6$ alkyl.

41. The method of claim 40 wherein the compound is N-(2-chloro-4-methylphenyl)-N-(4,5-dihydro-2-thiazolyl)-[(3-pyridyl)methyl]amine.

42. The method of claim 40 wherein the compound is N-(2-methyl-4-chlorophenyl)-N-(4,5-dihydro-2-thiazolyl)-[(3-pyridyl)methyl]amine.

43. A method of claim 37 wherein $R^5$ is

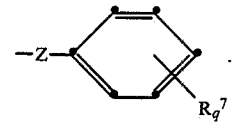

44. A method of claim 43 wherein Z is oxygen.

45. The method of claim 44 wherein the compound is N-(4-phenoxyphenyl)-N-(4,5-dihydro-2-thiazolyl)-[(3-pyridyl)methyl]amine.

46. A composition comprising an agriculturally acceptable carrier and from about 0.1 to about 95.0 percent by weight of a compound of claim 1.

47. The composition of claim 46 wherein the compound is N-(4-chlorophenyl)-N-(4,5-dihydro-2-thiazolyl)-[(3-pyridyl)methyl]amine.

48. The composition of claim 46 wherein the compound is N-(2,4-dichlorophenyl)-N-(4,5-dihydro-2-thiazolyl)-[(3-pyridyl)methyl]amine.

49. The composition of claim 48 wherein the compound is N-(4-chlorophenyl)-N-(4,5-dihydro-2-thiazolyl)-[1-(3-pyridyl)ethyl]amine.

50. The composition of claim 48 wherein the compound is N-(2-chloro-4-methylphenyl)-N-(4,5-dihydro-2-thiazolyl)-[(3-pyridyl)methyl]amine.

51. The composition of claim 48 wherein the compound is N-(2-methyl-4-chlorophenyl)-N-(4,5-dihydro-2-thiazolyl)-[(3-pyridyl)methyl]amine.

52. The composition of claim 48 wherein the compound is N-(4-phenoxyphenyl)-N-(4,5-dihydro-2-thiazolyl)-[(3-pyridyl)methyl]amine.

53. The composition of claim 48 wherein the compound is N-(2,4-difluorophenyl)-N-(4,5-dihydro-2-thiazolyl)-[(3-pyridyl)methyl]amine.

54. The composition of claim 48 wherein the compound is N-(4-chlorophenyl)-N-(4,5-dihydro-4-methyl-2-thiazolyl)-[1-(3-pyridyl)ethyl]amine.

* * * * *